United States Patent [19]

Ichikawa et al.

[11] 4,209,644
[45] Jun. 24, 1980

[54] ALLYL ACETYL DERIVATIVES OF β, γ-UNSATURATED ALDEHYDE

[75] Inventors: Yataro Ichikawa, Iwakuni; Teizo Yamaji, Yamaguchi; Mamoru Yamamoto, Iwakuni, all of Japan

[73] Assignee: Teijin Limited, Osaka, Japan

[21] Appl. No.: 856,179

[22] Filed: Nov. 30, 1977

Related U.S. Application Data

[63] Continuation of Ser. No. 735,954, Oct. 27, 1976, abandoned, which is a continuation of Ser. No. 496,833, Aug. 12, 1974, abandoned.

[30] Foreign Application Priority Data

| Aug. 16, 1973 | [JP] | Japan | 48-91280 |
| Oct. 2, 1973 | [JP] | Japan | 48-110179 |
| Oct. 5, 1973 | [JP] | Japan | 48-112114 |
| Nov. 21, 1973 | [JP] | Japan | 48-130109 |

[51] Int. Cl.² ............... C07C 43/30; C11B 9/00
[52] U.S. Cl. ............. 568/596; 568/486; 568/426; 568/420; 568/447; 260/347.8; 568/592; 568/591; 549/66; 252/522 R
[58] Field of Search ........... 260/615 A; 568/596

[56] References Cited

U.S. PATENT DOCUMENTS

| 2,501,144 | 3/1950 | Saunders | 260/615 A |
| 2,947,786 | 8/1960 | Brannock | 260/615 A |
| 3,978,092 | 8/1976 | Ichikawa et al. | 260/615 A X |
| 4,016,212 | 4/1977 | Leimgruber et al. | 260/615 A X |

*Primary Examiner*—Howard T. Mars
*Attorney, Agent, or Firm*—Sherman & Shalloway

[57] ABSTRACT

An unsaturated carbonyl compound, for example, one expressed by the following formula,

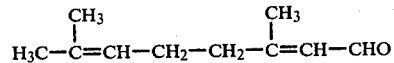

is prepared by maintaining at an elevated temperature a novel allyl acetal of a β,γ-unsaturated aldehyde, for example, one expressed by the following formula

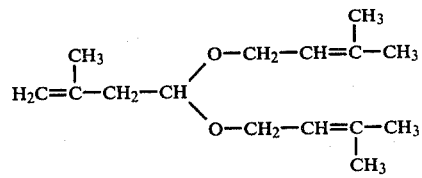

The allyl acetal can be derived, for example, for 3-methyl-3-butenal-1 having 5 carbon atoms and prenyl alcohol having 5 carbon atoms. Thus, the unsaturated aldehyde having the increased number of carbon atoms can be formed in a high yield by a relatively simple reaction.

5 Claims, No Drawings

ALLYL ACETYL DERIVATIVES OF $\beta$, $\gamma$-UNSATURATED ALDEHYDE

This is a continuation of application Ser. No. 735,954 filed Oct. 27, 1976, now abandoned, which in turn is a continuation of application Ser. No. 496,833 filed Aug. 12, 1974, now abandoned.

This invention relates to a process for the preparation of unsaturated carbonyl compounds. More particularly, the invention relates to a process for the preparation of unsaturated aldehydes containing an increased number of carbon atoms, from $\beta,\gamma$-unsaturated aldehydes or derivatives thereof, with allyl alcohol, or from the allyl acetal derivatives of $\beta,\gamma$-unsaturated aldehyde. The invention furthermore relates to the novel allyl acetal derivatives of $\beta,\gamma$-unsaturated aldehyde.

The novel allyl acetal derivatives of $\beta,\gamma$-unsaturated aldehyde provided by the invention are themselves useful as perfume, and also are important intermediates in the preparation of unsaturated aldehyde containing an increased number of carbon atoms. Again, the unsaturated aldehyde containing the increased number of carbon atoms formed in accordance with the invention (which will be hereinafter referred to simply as the unsaturated aldehyde for convenience) is a valuable compound in the terpene chemical industries, particularly as perfume, medicines, pesticides, or the intermediate products therefor.

Such unsaturated carbonyl compounds have been heretofore prepared through cumbersome procedures. For example, first carbonyl compounds and acetylene are used to form acetylene alcohols which are then reduced to the corresponding alcohols, and the alcohols are reacted with diketene, acetoacetic ester, isopropenyl ether, or the like (U.S. Pat. Nos. 2,516,826, 2,628,250, 2,638,484).

Such conventional process requires a large number of reaction steps because, for example, five carbon atoms are to be added to the starting carbonyl compound. Furthermore, the use of acetylene, which is difficult to handle, as the reactant inevitably renders the process industrially disadvantageous.

According to the present invention, simply by maintaining the allyl acetal derivatives of the formula below,

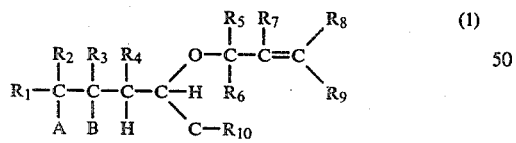

wherein $R_1$, $R_2$, $R_3$, $R_4$, $R_5$, $R_6$, $R_7$, $R_8$, and $R_9$, which may be the same or different, denote hydrogen or a monovalent organic group, $R_{10}$ stands for hydrogen, a monovalent organic group, or a monovalent acid residue, the monovalent organic group being optionally the same as the atomic group of the formula,

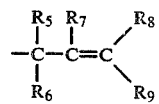

furthermore, any two of $R_1$, $R_2$, $R_3$, and $R_4$ may together form an alicyclic ring, aromatic ring, or heterocyclic ring containing hetero atoms, also any set of $R_5$ and $R_7$, $R_7$ and $R_8$, $R_8$ and $R_9$, and $R_5$ and $R_8$ may together form an aliphatic ring, or a heterocyclic ring containing hetero atoms, and A and B are the groups which either together form a double bond between the carbons at $\beta$- and $\gamma$-positions, or can form a double bond between carbons as eliminated, at an elevated temperature, the unsaturated aldehydes of the formula (2) below,

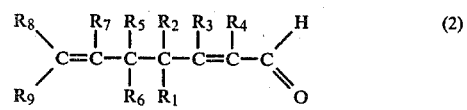

in which $R_1$, $R_2$, $R_3$, $R_4$, $R_5$, $R_6$, $R_7$, $R_8$, and $R_9$ have the previously given definitions,
are formed.

The allyl acetal derivatives of the formula (1) are novel compounds. According to the invention, the novel allyl acetal derivatives can be readily derived from $\beta,\gamma$-unsaturated aldehyde of the formula (3) below,

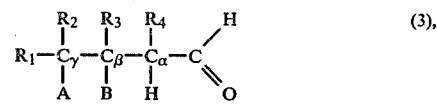

$R_1$, $R_2$, $R_3$, and $R_4$ may be the same or different, each denoting hydrogen or a monovalent organic group inert to the reaction, any two of $R_1$, $R_2$, $R_3$, and $R_4$ may optionally form an alicyclic ring, aromatic ring, or a heterocyclic ring containing hetero atoms, and A and B are the groups which either together form a double bond between the carbons at $\beta$- and $\gamma$-positions, or can form a double bond between the carbons as eliminated.

In the aldehydes of the formula (3), either the two carbon atoms at $\beta$- and $\gamma$-positions to the carbonyl group

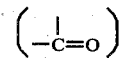

are linked by a double bond, or these two carbon atoms are bonded with the groups which can form a double bond. Therefore, the aldehydes covered by the formula (3) are collectively referred to as "$\beta,\gamma$-unsaturated aldehydes" in the present specification.

We believe that the reactions for forming the unsaturated aldehydes of the formula (2) from the $\beta,\gamma$-unsaturated aldehydes of formula (3), or the allyl acetal derivatives of formula (1) derived from such unsaturated aldehydes, i.e., the allyl acetal derivatives of the $\beta,\gamma$-unsaturated aldehydes, have never before been disclosed in any of literature, and are novel reactions.

According to the invention, from the $\beta,\gamma$-unsaturated aldehydes of formula (3) and the allyl alcohol of formula (4) below,

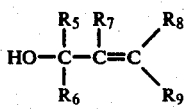

in which
R$_5$, R$_6$, R$_7$, R$_8$, and R$_9$ may be the same or different, each denoting hydrogen or a monovalent organic group, and any set of R$_5$ and R$_7$, R$_7$ and R$_8$, R$_8$ and R$_9$, and R$_5$ and R$_8$ may together form an alicyclic ring, or a heterocyclic ring containing hetero atoms, the unsaturated aldehydes containing an increased number of carbon atoms, of the formula (2) can be formed through simple procedures and furthermore in a high yield.

In other words, according to the invention, from the unsaturated aldehyde skeletons of the formula (3a) below,

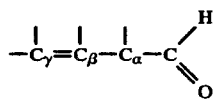

(or the skeletons capable of forming the above), the unsaturated aldehyde skeletons containing the increased number of carbon atoms, of the formula (2a) below,

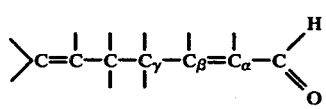

can be advantageously formed through simple procedures and in the high yield.

Thus, it is apparent that the process of this invention is by far superior to the already described conventional process using acetylene. Hereinafter the invention will be described in further details.

[I-1] Method for making the unsaturated aldehyde (No. 1)

According to the invention, by maintaining the allyl acetal derivatives of the formula (1) below,

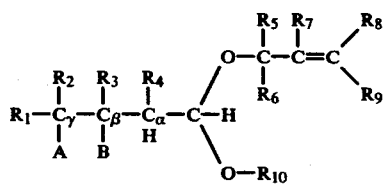

in which R$_1$, R$_2$, R$_3$, R$_4$, R$_5$, R$_6$, R$_7$, R$_8$, R$_9$, R$_{10}$, A, and B have the previously given definitions,
at an elevated temperature as aforesaid, the unsaturated aldehyde of the formula (2) below,

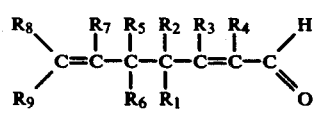

in which R, R$_1$, R$_2$, R$_3$, R$_4$, R$_5$, R$_6$, R$_7$, R$_8$, and R$_9$ have the already given definitions can be formed.

As the allyl acetal derivatives of the formula (1), those of which R$_1$, R$_2$, R$_3$, R$_4$, R$_5$, R$_6$, R$_7$, R$_8$ and R$_9$ may be the same or different, each being selected from the group consisting of hydrogen and organic groups of 1 to 45 carbon atoms; R$_{10}$ is selected from the group consisting of hydrogen, hydrocarbon residues of 1 to 20 carbon atoms, and organic acid residues of 1 to 20 carbon atoms; any two of R$_1$, R$_2$, R$_3$, and R$_4$ optionally forming together an alicyclic ring, or a heterocyclic ring containing hetero atoms, and furthermore, any set of R$_5$ and R$_7$, R$_7$ and R$_8$, R$_8$ and R$_9$, or R$_5$ and R$_8$ optionally forming together an aliphatic ring, or a heterocyclic ring containing hetero atoms, and A and B are the groups which either are together forming a double bond between the carbons at β- and γ-positions, or either one of them is selected from the group consisting of alkoxy groups and organic acid residues of both 1 to 20 carbon atoms, and the other is hydrogen, referring to the formula (1), are preferred.

Of the allyl acetal derivatives of the formula (1), particularly the allyl acetal derivatives covered by the formula (1-a) below,

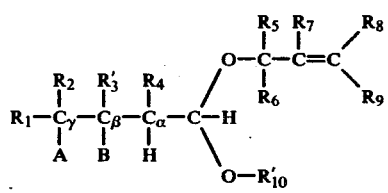

in which
R'$_3$ is a monovalent organic group of 1 to 45 carbon atoms,

R$_1$, R$_2$, R$_4$, R$_5$, R$_6$, R$_7$, R$_8$, and R$_9$ may be same or different each being selected from the group consisting of hydrogen and monovalent organic groups of 1 to 45 carbon atoms, any two of R$_1$, R$_2$, R$_3$, and R$_4$ optionally forming together an alicyclic ring, or a heterocyclic ring containing hetero atoms, and furthermore, any set of R$_5$ and R$_7$, R$_7$ and R$_8$, R$_8$ and R$_9$, and R$_5$ and R$_8$, optionally forming together an aliphatic ring, or a heterocyclic ring containing hetero atoms, R'$_{10}$ is selected from the group consisting of hydrogen, and saturated or unsaturated hydrocarbon residues of 1 to 20 carbon atoms, and A and B are the groups which either are together forming a double bond between the carbon at β- and γ-positions, or either one of them is selected from the group consisting of alkoxy groups and organic acid residues of both 1 to 20 carbons, the other being hydrogen, are advantageously used.

According to the invention, the allyl acetal derivatives of the formula (1), preferably of the formula (1-a), are subjected to dealcohol rearrangement or deacid rearrangement, to form the unsaturated aldehydes of the formula (2).

The reaction conditions, therefore, are not critical so far as they allow the occurrence of said dealcohol rearrangement or deacid rearrangement.

The above reaction to make the unsaturated aldehydes (2) from the allyl acetal derivatives (1) can progress in the absence of catalyst, but the presence of suitable catalyst assists the formation of the object unsaturated aldehydes at higher conversion and selectivity.

The reaction can be practiced either in vapor phase or liquid phase, but normally the liquid phase is preferred. In the latter case, presence of solvent is optional, while use of solvent is preferred. The type of the solvent is not critical, so far as it is inert to the reaction of the invention and itself stable under the reaction conditions of the invention. Examples of preferred solvents include the following:

(I) Aliphatic hydrocarbons:

Aliphatic hydrocarbons of 1 to 40 carbon atoms, preferably of 1 to 20 carbon atoms, such as propane, butane, pentane, hexane, heptane, and octane;

(II) Alicyclic hydrocarbons:

Alicyclic hydrocarbon of 3 to 40 carbon atoms, preferably of 5 to 20 carbon atoms, such as cyclohexane, methylcyclohexane, ethylcyclohexane, and decaline;

(III) Aromatic hydrocarbons:

Aromatic hydrocarbons of 6 to 40 carbon atoms, preferably of 6 to 20 carbon atoms, such as benzene, toluene, xylene (ortho-, meta-, para-), cumene, and tetraline;

(IV) Halogenated hydrocarbons:

Halogenated hydrocarbons of 1 to 40 carbon atoms, preferably of 1 to 20 carbon atoms, such as carbon tetrachloride, methylene dichloride, chloroform, dichloroethane, trichloroethane, tetrachloroethane, chlorobenzene, and dichlorobenzene;

(V) Ethers:

Ethers of 2 to 40 carbon atoms, preferably of 2 to 20 carbon atoms, such as diethylether, tetrahydrofuran, and dioxane;

(VI) Esters:

Esters of 2 to 40 carbon atoms, preferably of 2 to 30 carbon atoms, such as ethyl acetate, butyl acetate, methyl benzoate, dimethyl phthalate, diethyl phthalate, and dibutyl phthalate.

Of the above-named solvents, particularly the (I) aliphatic hydrocarbons and (III) aromatic hydrocarbons are preferred.

The reaction to form the unsaturated aldehydes (2) from the allyl acetal derivatives (1) or (1-a) can be performed by maintaining said allyl acetal derivatives (1) or (1-a) at an elevated temperature normally within the range of the normal to 500° C., preferably 100°–400° C., particularly 150°–350° C. The reaction pressure may be reduced, atmospheric, or elevated.

The reaction time varies depending on the reaction temperature and reaction phase, i.e., either vapor or liquid, but normally it is no shorter than 1 second. In the liquid phase reaction, it is normally from 10 seconds to 100 hours, preferably 30 seconds to 70 hours, particularly 1 minute to 10 hours.

The reaction may be practiced either batchwise or continuously.

When the above reaction is practiced in the presence of an acid catalyst, furthermore, it becomes possible to form the object unsaturated aldehyde at still higher conversions and selectivities, normally within the shortened reaction time.

As the acid catalyst, any of those which show acidity may be used, including, for example, inorganic acid, organic acid, solid acid, and strong acid salt of weakly basic substance.

Specific examples of such acid catalyst include inorganic acids such as hydrochloric acid, nitric acid, sulfuric acid, perchloride, phosphoric acid, boric acid, titanic acid, hypophosphorous acid, and metaboric acid. Also the examples of organic acid catalyst include aliphatic carboxylic acids such as formic, acetic, propionic, butyric, monochloroacetic, dichloroacetic, trichloroacetic, stearic, palmitic, acrylic, oxalic, tartaric, and maleic acids; alicyclic carboxylic acids, such as hexahydrobenzoic acid and naphthenic acid; aromatic carboxylic acids such as benzoic, o-, m- and p-toluic, phthalic, isophthalic, terephthalic, trimellitic, α- and β-naphthoic, anisic, chlorobenzoic, nitrobenzoic, cyanobenzoic, and bromobenzoic acids; aliphatic, alicyclic, or aromatic sulfonic acids such as methanesulfonic, ethanesulfonic, cyclohexanesulfonic, benzenesulfonic, and p-toluenesulfonic acids; and phosphinic or phosphonic acids such as methylphosphinic, ethylphosphinic, phenylphosphinic, methylphosphonic, ethylphosphonic, and benzylphosphonic acids. As the solid acid catalyst, besides the oxide type solid acid such as silica gel, silica-alumina, alumina, titanium oxide, germanium oxide, and boron oxide, those carried on salt or acid, such as $NH_4Cl$- carried silica-alumina, and zinc chloride-carried silica-alumina, can be named. Furthermore, examples of strong acid salt of weakly basic substance include ammonium chloride, ammonium nitrate, ammonium sulfate, ammonium phosphate, ferric chloride, zinc chloride, aluminum chloride, calcium chloride, tin chloride, palladium chloride, ammonium p-toluenesulfonate, and triethylammonium p-toluenesulfonate. The foregoing are only given as examples, and it should be obvious that the scope of this invention is by no means thereby limited.

The acid catalyst employed in the subject process preferably has an acid strength (pKa) within the range of 0 to 10, particularly from 0 to 7, inter alia, from 0 to 5.

Of the above-named acid catalysts, those having the pKa of 0 to 3 are the optimum for the purpose of this invention. Specific examples of such acid catalysts are: hydrochloric, nitric, sulfuric, trichloroacetic, methanesulfonic, ethanesulfonic, cyclohexanesulfonic, benzenesulfonic, and p-toluenesulfonic acids.

The suitable amount of the acid catalyst is no more than 500 mol % per mol of the β,γ-unsaturated aldehydes of the formula (3) or allyl acetals (1), preferably no more than 250 mol %, inter alia, no more than 100 mol %. The lower limit is no less than $1 \times 10^{-6}$ mol %, preferably no less than $1 \times 10^{-5}$ mol %.

According to the invention, it is possible to form the object unsaturated aldehydes (2) from the allyl acetal derivatives (1), preferably (1-a), in the yield of 90–95%, or even higher, under the preferred reaction conditions employing the acid catalyst.

As the allyl acetal derivatives to be used as the starting material in the above reaction, those of the formula (1-a$_1$), particularly those covered by the following formula (1-a), through (1-a$_6$) are preferred.

$$\text{(1)} \quad R_1-C_\gamma=C_\beta-C_\alpha-C-H \quad \begin{array}{c} R_5 \\ | \\ O=C- \end{array} \begin{array}{c} R_7 \\ | \\ C= \end{array} C \begin{array}{c} R_8 \\ / \\ \diagdown \\ R_9 \end{array} \quad (1\text{-}a_1)$$

-continued

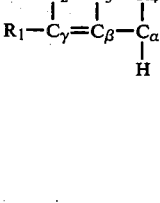

(1-a2)

(2) $R_1-C_\gamma=C_\beta-C_\alpha-C-H$ ...

(1-a3)

(3) ...

(1-a4)

(4) ...

(1-a5)

(5) ...

(1-a6)

(6) ...

In the above formulae, R in the formulae (1-a₁), (1-a₃), and (1-a₄) is selected from the alkyl groups of 1 to 10 carbons, preferably 1 to 5 carbons; —OR' in the formulae (1-a₃), (1-a₄), (1-a₅) and (1-a₆) stands for an alkoxy group of 1 to 5 carbons; $R_1$, $R_2$, $R_3$, $R_4$, $R_5$, $R_6$, $R_7$, and $R_8$ in the formulae (1-a₁) through (1-a₆), and $R_{11}$, $R_{12}$, $R_{13}$, $R_{14}$, and $R_{15}$ in the formulae (1-a₂), (1-a₅), and (1-a₆) may be same or different, each being selected from the group consisting of hydrogen and hydrocarbon residues of 1 to 45 carbon atoms.

In the above formulae (1-a₁) through (1-a₆), any two of $R_1$, $R_2$, $R_3$, and $R_4$ may be together forming an alicyclic ring, or a heterocyclic ring containing at least one hetero atom such as, for example, oxygen, sulfur, or nitrogen. Preferred cases are those in which such a ring is formed by $R_1$ and $R_2$.

Furthermore, any set of $R_5$ and $R_7$, $R_7$ and $R_8$, $R_8$ and $R_9$, $R_5$ and $R_8$, or $R_{11}$ and $R_{13}$, $R_{13}$ and $R_{14}$, $R_{14}$ and $R_{15}$, or $R_{11}$ and $R_{14}$, may be together forming an alicyclic ring, or a heterocyclic ring containing at least one hetero atom such as, for example, oxygen, sulfur, or nitrogen.

When the allyl acetal derivatives of the formulae (1-a₁) through (1-a₆) contain such alicyclic, aromatic, or heterocyclic ring, preferred examples of such rings include the following: cycloheptane; cyclohexane, cyclohexene, benzene, pyridine, piperidine, piperazine, furan, pyrrolidine, thiophene, and hydroxythiazole rings.

In the above formulae (1-a₂), (1-a₅), and (1-a₆), if the atomic group of the formula (Y₁) below,

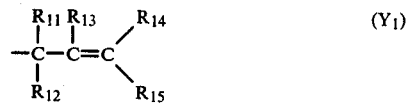

(Y₁)

is identical with the atomic group of the formula (Y₂),

(Y₂)

the unsaturated aldehyde of the formula (2) below can be obtained:

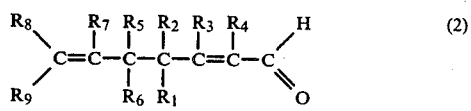

(2)

in which $R_1$, $R_2$, $R_3$, $R_4$, $R_5$, $R_6$, $R_7$, $R_8$, and $R_9$ have already given definitions.

However, if the two atomic groups Y₁ and Y₂ are different, the product is a mixture of the unsaturated aldehyde of the above formula (2) and that of the formula (2-a) below:

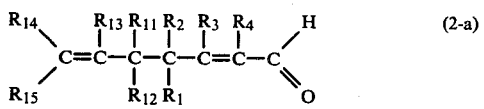

(2-a)

in which $R_1$, $R_2$, $R_3$, $R_4$, $R_{11}$, $R_{12}$, $R_{13}$, $R_{14}$, and $R_{15}$ have the already given definitions.

The forming ratio of the two components is approximately determined by the reactivity between the two atomic groups Y₁ and Y₂. Normally it is preferred that the two atomic groups should be identical.

As the allyl acetal derivatives of the formula (1), preferably (1-a), inter alia, of the formula (1-a₁)–(1-a₆), those in which the carbon atom at β-position to the acetal bond

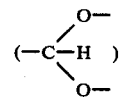

is substituted with an organic group, preferably a hydrocarbon residue, (—R'₃) of 1 to 20, preferably 1 to 10, carbon atoms, are advantageously used. Also in those formulae, $R_1$, $R_2$, $R_4$, $R_5$, $R_6$, $R_7$, $R_8$, $R_9$, $R_{11}$, $R_{12}$, $R_{13}$, $R_{14}$, and $R_{15}$ are preferably hydrogen or hydrocarbon residues of 1 to 20 carbon atoms, inter alia, the hydrocarbon residues of 1 to 10 carbon atoms such as methyl, ethyl, propyl, butyl, amyl, and hexyl groups.

In the foregoing formula (1) or (1-a), furthermore, A and B are preferably forming a double bond. If otherwise, it is preferred that either one of A and B is an alkoxy group of the formula —OR' (R' being preferably selected from alkyl groups of 1 to 5 carbon atoms), and the other is hydrogen.

When the atomic group of the formula,

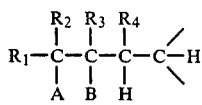

in the formula (1) or (1-a) is expressed by X, preferred specific examples of the X are as follows, given together with those of the aforesaid atomic group $-Y_1$ (or $Y_2$).

Examples of X-group

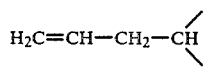 (X-1)

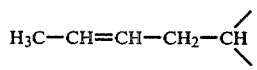 (X-2)

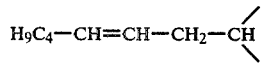 (X-3)

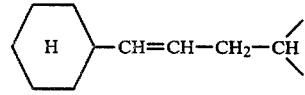 (X-4)

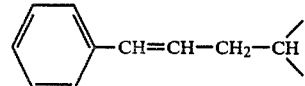 (X-5)

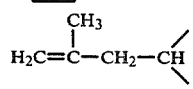 (X-6)

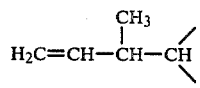 (X-7)

Examples of $Y_1$ (or $Y_2$)

$-CH_2-CH=CH_2$ (Y$_1$-1)

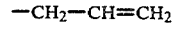 (Y$_1$-2)

$-CH_2-CH=CH-CH_3$ (Y$_1$-3)

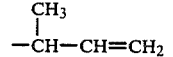 (Y$_1$-4)

 (Y$_1$-5)

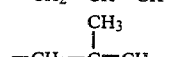 (Y$_1$-6)

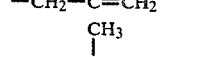 (Y$_1$-7)

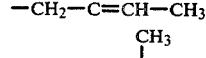 (Y$_1$-8)

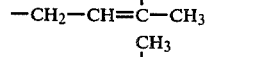 (Y$_1$-9)

(n = 1–10, preferably 1–5)

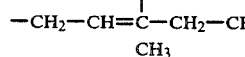

(n = 1–10, preferably 1–5)

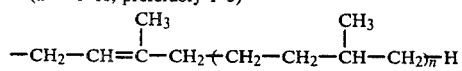 (Y$_1$-10)

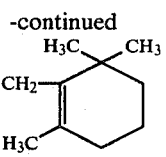 (Y$_1$-11)

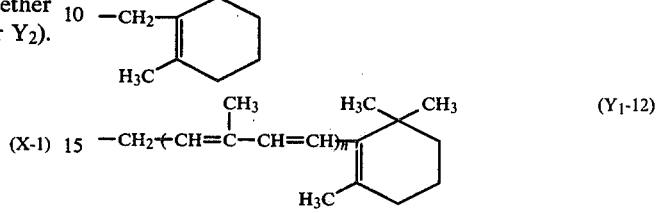 (Y$_1$-12)

(n = 1–10 preferably 1–5)

$-CH_2-\substack{\square\\O}$ (Y$_1$-13)

$-CH_2-\substack{\square\\O}$ (Y$_1$-14)

$-CH_2-\substack{\square\\S}$ (Y$_1$-15)

$-CH_2-\substack{\square\\S}$ (Y$_1$-16)

If $-O-R_{10}$ of the formula,

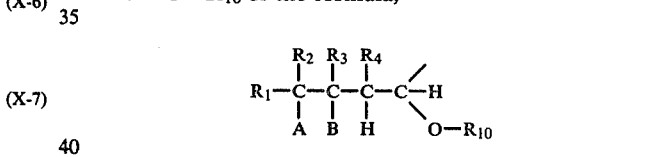

in the formula (1) or (1-a) is expressed by Z, examples of preferred specific Z are as follows:

Examples of Z

—OH $-OCH_3, -OC_2H_5, -OC_3H_7, -OC_4H_9,$ $-OC_5H_{11}, -OC_{10}H_{21}$

—OCOCH$_3$,

[I-2] Preparation of the allyl acetal derivatives:

The allyl acetal derivatives of the formula (1) or (1-a) can be synthesized through various methods, several examples of which are described hereinbelow.

Method A

Upon reacting the β,γ-unsaturated aldehyde of the formula (3) below,

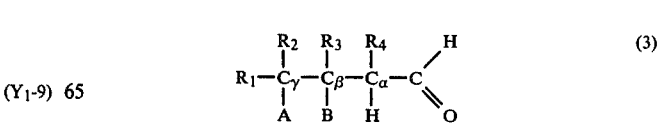 (3)

in which $R_1$, $R_2$, $R_3$, and $R_4$ may be dame or different, each denoting hydrogen or a monovalent organic group inert to the reaction, any two of the $R_1$ through $R_4$ optionally forming together an alicyclic ring, or a heterocyclic ring containing hetero atoms, and A and B are the groups which either are together forming a double bond between the carbons at $\beta$- and $\gamma$-positions, or can form a double bond between said carbons as eliminated, with allyl alcohol of the formula (4) below,

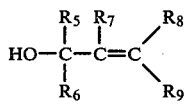   (4)

in which $R_5$, $R_6$, $R_7$, $R_8$, and $R_9$ may be same or different, each denoting hydrogen or a monovalent organic group inert to the reaction, any set of $R_5$ and $R_7$, $R_7$ and $R_8$, $R_8$ and $R_9$, and $R_5$ and $R_8$, optionally forming together an aliphatic ring, or a heterocyclic ring containing hetero atoms, the allyl acetal derivatives of the formula (5) below

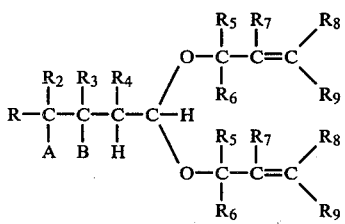   (5)

in which $R_1$, $R_2$, $R_3$, $R_4$, $R_5$, $R_6$, $R_7$, $R_8$, $R_9$, A, and B have the previously given definitions, are formed. The appropriate temperature for this acetal formation reaction differs depending on the presence or absence of catalyst, reaction time, method of the separation of the produced water and the like, the reaction conditions being not critical so far as the reaction progresses smoothly.

The reaction, however, is preferably performed, for example, at the temperatures not exceeding 130° C., preferably 80°–120° C., in the preferred presence of an acid catalyst, while eliminating the water formed upon the reaction out of the reaction system. Thus, the allyl acetal derivatives (1) or (1-a) can be formed in such a high yield as 95%, or even higher.

As the acid catalyst, the same group of compounds named as the useful catalyst for the preparation of unsaturated aldehyde in the foregoing section [I-1] may be used, particularly preferred catalysts being the acids having the pKa not higher than 5, inter alia, not higher than 3, and ammonium salts and organic amine salts of such acids.

Method B

Again the alkyl acetal derivatives of the formula (1) or (1-a) may be formed by the steps comprising reacting the $\beta,\gamma$-unsaturated aldehyde of the formula (3), for example, with a monohydric alcohol of the formula (6) below,

HO—$R_{16}$   (6)

in which $R_{16}$ is selected from the organic groups of 1 to 20 carbon atoms, and/or an organic acid of the formula (7) below or a reactive derivative thereof,

HO—$R_{17}$   (7)

in which $R_{17}$ is selected from organic acid residues of 1 to 20 carbon atoms, to form the acetal or ester of $\beta,\gamma$-unsaturated aldehyde expressed by the formula (8) below,

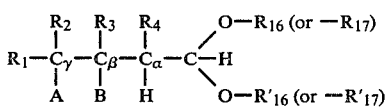   (8)

in which $R_1$, $R_2$, $R_3$, $R_4$, A, B, $R_{16}$, and $R_{17}$ have the previously given definitions, $R'_{16}$ is selected from the group consisting of hydrogen and the monovalent organic groups of 1 to 20 carbon atoms same to $R_{16}$, and $R'_{17}$ is selected from the group consisting of hydrogen and the monovalent organic groups of 1 to 20 carbon atoms same to $R_{17}$, and then, after optional isolation of said acetal or ester, reacting the same with the allyl alcohol of formula (4).

The acetal of $\beta,\gamma$-unsaturated aldehyde of above formula (8) can be formed under the conventional acetal-forming reaction conditions which are known per se. For example, said acetal can be readily formed in the high yield by reacting the $\beta,\gamma$-unsaturated aldehyde of formula (3) with the alcohol of formula (6), i.e., HO—$R_{16}$, for example $-50°$ to 150° C., preferably at 0° C. to 130° C., particularly preferably at room temperature to 100° C., advantageously in the presence of the already described acid catalyst. Again, upon contacting thus formed acetal of formula (8) further with an allyl alcohol of formula (4), for example, at the temperatures not higher than 130° C., preferably from room temperature to 120° C., favorably in the presence of the described acid catalyst, more advantageously concurrently distilling the eliminated alcohol off from the system, the allyl acetal derivatives of the formula (1) or (1-a) can be formed.

Whereas, the esters of $\beta,\gamma$-unsaturated aldehydes of the formula (8) are formed by reacting the $\beta,\gamma$-unsaturated aldehyde of formula (3) with the organic acid of formula (7), i.e., HO—$R_{17}$, preferably with the reactive derivatives thereof. As the "reactive derivatives of organic acid", for example, anhydrides and pyridinium salts of the organic acids are preferred. The resulting ester then is reacted with the allyl alcohol of formula (4), preferably in the presence of an inorganic or organic salt, for example, an acid acceptor such as sodium carbonate or organic amine, to form the allyl acetal derivatives of formula (1) or (1-a).

Method C

The $\beta,\gamma$-unsaturated aldehyde of formula (3),

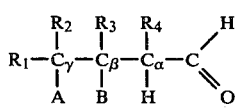   (3)

in which $R_1$, $R_2$, $R_3$, $R_4$, A, and B have the previously given definitions,
may be reacted with the monohydric alcohol of formula (6),

$$HO-R_{16} \qquad (6)$$

in which $R_{16}$ has the previously given definition, or the organic acid of formula (7),

$$HO-R_{17} \qquad (7)$$

in which $R_{17}$ has the previously given definition, preferably the reactive derivatives thereof such as an anhydride of said organic acid, and also with the allyl alcohol of formula (4),

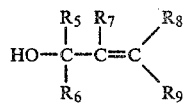

in which $R_5$, $R_6$, $R_7$, $R_8$, and $R_9$ have the previously given definitions,
to form the allyl acetal of formula (9),

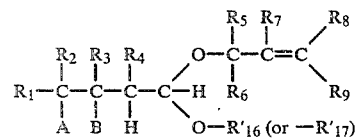

in which
$R_1$, $R_2$, $R_3$, $R_4$, $R_5$, $R_6$, $R_7$, $R_8$, $R_9$, A, B, $R_{16}$ and $R_{17}$ have the previously given definitions,
$R'_{16}$ is selected from the group consisting of hydrogen and monovalent organic groups of 1 to 20 carbons same to $R_{16}$ and
$R'_{17}$ is selected from the group consisting of hydrogen and monovalent organic groups of 1 to 20 carbons same to $R_{17}$.

This reaction again is performed preferably in the presence of already described acid catalyst, for example, at the temperatures not higher than 130° C.

In the above reaction, depending on the mol ratio between the employed monohydric alcohol of formula (6) or the reactive derivatives of organic acid of formula (7), for example, anhydride thereof, and the allyl alcohol of formula (4), concurrently the diallyl acetal of the $\beta,\gamma$-unsaturated aldehyde may be formed. Or, monohydric alcohol-acetal of said aldehyde, or the diester thereof, may be concurrently formed.

Method D

The diallyl acetal of $\beta,\gamma$-unsaturated aldehyde covered by the formula (5) may also be formed by reacting the allyl acetal of formula (9) with the allyl alcohol of formula (4).

This reaction easily progresses under the reaction conditions already described, preferably in the presence of the acid catalyst, at the temperatures, for example, ranging from room temperature to 120° C.

Method E

Furthermore, the allyl acetal derivatives of the formula (1) can be formed by the steps comprising reacting the $\beta,\gamma$-unsaturated aldehyde of formula (3) with an alkyl ester of, for example, ortho-formic acid, silicic acid, and the like, at moderate temperatures, preferably in the presence of a catalyst composed of ammonium salt of a strong acid such as sulfuric acid or nitric acid, to first form dialkyl acetal of the $\beta, \gamma$-unsaturated aldehyde, and reacting the acetal with allyl alcohol of the formula (4). The other acetal formation methods except for the above-mentioned methods A through E can also be used in our process.

Of the above-mentioned methods A through E, the methods A and B are advantageous.

[II] Preparation of the unsaturated aldehyde (No. 2)

According to the invention, as is apparent from the foregoing descriptions, the allyl acetal derivatives of formula (1), preferably of formula (1-a), inter alia, the formula (1-a$_1$) through (1-a$_6$), are formed by any of the methods, A through E, which are convertible to the object unsaturated aldehyde of formula (2) when maintained at elevated temperatures, as mentioned in the foregoing section [I-1]. Before the conversion, the allyl acetal derivatives are optionally separated from the reaction mixture.

Thus, according to the invention, either [II-1a] the $\beta,\gamma$-unsaturated aldehyde of the formula (3),

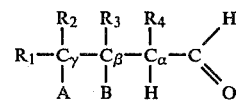

in which
$R_1$, $R_2$, $R_3$, and $R_4$, may be same or different, each denoting hydrogen or a monovalent organic group inert to the reaction, any two of $R_1$, $R_2$, $R_3$, and $R_4$ optionally together forming an alicyclic ring, or a heterocyclic ring containing hetero atoms, and
A and B are the groups which either are together forming a double bond between the carbon at $\beta$- and $\gamma$-positions, or can form a double bond between said carbons as eliminated,
is reacted with allyl alcohol of the formula (4) below,

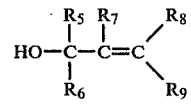

in which
$R_5$, $R_6$, $R_7$, $R_8$, and $R_9$ may be same or different, each denoting hydrogen or a monovalent organic group inert to the reaction,
any set of $R_5$ and $R_7$, $R_7$ and $R_8$, $R_8$ and $R_9$, or $R_5$ and $R_8$, optionally forming together an aliphatic ring, or a heterocyclic ring containing hetero atoms,
or
[II-1] the $\beta,\gamma$-unsaturated aldehyde is reacted with the allyl alcohol in the presence of the monohydric alcohol of formula (6),

$$HO-R_{16} \qquad (6)$$

in which $R_{16}$ is an organic group of 1 to 20 carbons, and/or the organic acid or reactive derivatives thereof, of the formula (7) below,

$$HO-R_{17} \qquad (7)$$

in which $R_{17}$ is a monovalent organic acid residue of 1 to 20 carbons, or

[II-1c] the β,γ-unsaturated aldehyde is first reacted with the monohydric alcohol of the formula, HO—R$_{16}$ and/or the organic acid or reactive derivatives thereof of the formula, HO—R$_{17}$, and thereafter with the allyl alcohol,
to form the allyl acetal derivatives of formula (1) below,

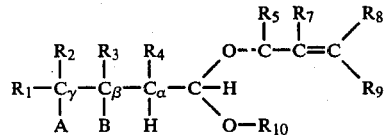  (1)

in which
R$_1$, R$_2$, R$_3$, R$_4$, R$_5$, R$_6$, R$_7$, R$_8$, R$_9$, A, and B have the previously given definitions, and
R$_{10}$ is selected from the group consisting of hydrogen, organic groups of 1 to 20 carbons and monovalent organic acid residues of 1 to 20 carbons.

[II-2] Thus formed allyl acetal derivatives are maintained at elevated temperatures, to form the unsaturated aldehyde of the formula (2) below:

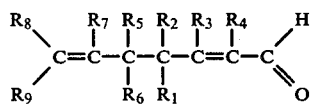  (2)

in which R$_1$, R$_2$, R$_3$, R$_4$, R$_5$, R$_6$, R$_7$, R$_8$, and R$_9$ have the previously given definitions.

Of the above-described methods, particularly preferred embodiments are such that (1) the β,γ-unsaturated aldehyde of formula (3) is reacted with the allyl alcohol of formula (4), or with the allyl alcohol and the monohydric alcohol of formula (6),

HO—R$_{16}$  (6)

in which R$_{16}$ has the previously given definition, to form the allyl acetal derivatives of formula (1),

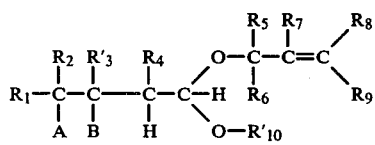  (1)

in which
R$_1$, R$_2$, R'$_3$, R$_4$, R$_5$, R$_6$, R$_7$, R$_8$, R$_9$, A, and B have the previously given definitions, and R'$_{10}$ denotes a saturated or unsaturated hydrocarbon residue of 1 to 20 carbons, which may be same with the atomic group of the formula,

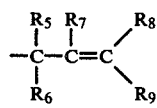

Or, (2) the β,γ-unsaturated aldehyde of the formula (3) is reacted with the monohydric alcohol formula (6) or the organic acid of the formula (7), preferably with the reactive derivatives of the organic acid, to form the acetal or ester of β,γ-unsaturated aldehyde expressed by the formula (8) below,

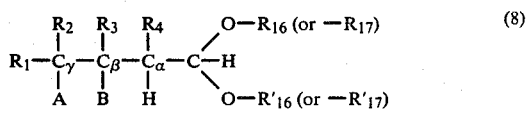  (8)

in which
R$_1$, R$_2$, R$_3$, R$_4$, A, B, R$_{16}$, R'$_{16}$, R$_{17}$ and R'$_{17}$ have the previously given definitions,
and the acetal or ester is further reacted with the allyl alcohol of formula (4) to form the allyl acetal derivatives of formula (1), preferably formula (1-a), which is subsequently converted to the unsaturated aldehyde of formula (2) as heated to elevated temperatures, preferably in the presence of an acid catalyst.

To the above-described reaction, the reaction conditions described in the foregoing sections [I-2] and [I-1] can be applied. In that occasion, the reaction for making the allyl acetal derivatives of formula (1), preferably (1-a), is preferably performed at the temperatures not exceeding 130° C. When the allyl acetal derivatives thus formed are led to the object unsaturated aldehyde of formula (2) without the intervening isolation from the reaction mixtures, the reaction is preferably continued until the ratio of either the β,γ-unsaturated aldehyde of formula (3) or the acetal or ester thereof of the formula (8) in the reaction system is reduced to no more than ⅔ mol per mol of the allyl acetal derivatives of formula (1), preferably (1-a), formed, and thereafter the allyl acetal derivatives are maintained at the elevated temperatures to be converted to the unsaturated aldehyde of formula (2).

Because, in the conversion of the allyl acetal derivatives to the unsaturated aldehyde of formula (2), the presence of an excessive amount of the unsaturated aldehyde of formula (3) and/or the acetal or ester thereof of formula (8), as the unreacted starting material, inhibits the formation of the object unsaturated aldehyde of formula (2).

The reaction to form the allyl acetal derivatives of formula (1) or (1-a) is advantageously performed at the temperatures not exceeding 130° C. as aforesaid, still more preferably at the temperatures ranging from room temperature to 120° C., particularly in the presence of aforesaid acid catalyst. Whereas, the reaction for converting the allyl acetal derivatives to the unsaturated aldehyde of formula (2) is effected at the temperature exceeding 130° C. with advantage, particularly at the temperatures not lower than 150° C. The preferred temperature range therefore is 150°–400° C., inter alia, 170°–350° C.

It is again advantageous to effect the second stage reaction to form the unsaturated aldehyde of formula (2) in the presence of the aforesaid acid catalyst, and also in the presence of the inert solvent mentioned in the foregoing section [I-1].

[III] Preparation of the unsaturated aldehyde (No. 3)

According to the invention, the unsaturated aldehyde of the formula (2) below,

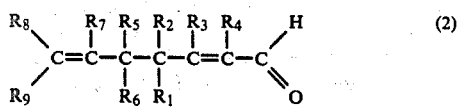

(2)

in which $R_1$, $R_2$, $R_3$, $R_4$, $R_5$, $R_6$, $R_7$, $R_8$, and $R_9$ have the previously given definitions, may also be formed by maintaining the β,γ-unsaturated aldehyde of formula (3) below,

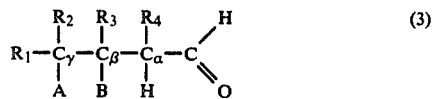

(3)

in which $R_1$, $R_2$, $R_3$, and $R_4$ may be same or different, each denoting hydrogen or a monovalent organic group inert to the reaction, any two of $R_1$, $R_2$, $R_3$, and $R_4$ optionally forming together an alicyclic ring, or heterocyclic ring containing hetero atoms, and A and B are the groups which either are together forming a double bond between the carbons at β- and γ-positions, or can form a double bond between said carbons as eliminated, or the acetal or ester thereof of the formula (10) below,

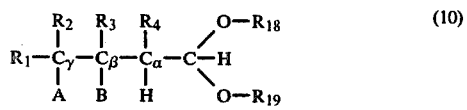

(10)

in which $R_1$, $R_2$, $R_3$, $R_4$, A, and B have the previously given definitions, and $R_{18}$ and $R_{19}$ may be same or different, each being selected from the group consisting of organic groups of 1 to b 20 carbons and organic acid residues of 1 to 20 carbons, it being permissible that either one of $R_{18}$ and $R_{19}$ is hydrogen.

together with the allyl alcohol of formula (4) below,

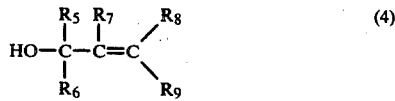

(4)

in which $R_5$, $R_6$, $R_7$, $R_8$, and $R_9$ have the previously given definitions, at elevated temperatures.

This process according to the invention is advantageous in that the object unsaturated aldehyde containing increased number of carbon atoms expressed by formula (2) can be formed through a single-stage reaction, by reacting the β,γ-unsaturated aldehyde of formula (3) or the acetal or ester of said aldehyde of formula (8), with the ally alcohol of formula (4).

In this process the suitable quantitative ratio of the reactants is normally no more than 100 mols, preferably no more than 50 mols, of the allyl alcohol per mol of the β,γ-unsaturated aldehyde of formula (3) or the acetalor ester thereof, of formula (8). The lower limit of the former is advantageously no less than 0.2 mol, preferably no less than 0.3 mol.

Presence of catalyst in the above reaction is not critical, but in the presence of acid catalyst the unsaturated aldehyde can be obtained in the better yield.

As the acid catalyst, any that exhibits acidity can be used, such as inorganic acids, organic acids, solid acids, strong acid salts of weakly basic substances, and the like, similar to those mentioned in the foregoing section [I-1]. Of such acid catalysts, those preferred have the acid strength (pKa) ranging from 0 to 10, preferably 0–7, inter alia, 0–5, as has been mentioned in [I-1].

Appropriate amount of the acid catalyst is no more than 500 mol %, preferably no more than 250 mol %, inter alia, no more than 100 mol %, per mol of the β,γ-unsaturated aldehyde of formula (3) and/or of the acetal and/or ester of the aldehyde, of formula (8). The lower limit is suitably no less than $1 \times 10^{-6}$ mol %, preferably no less than $1 \times 10^{-5}$ mol %.

The yield of the object unsaturated aldehyde of formula (2) is controlled mainly by the reaction temperature and time. It is also influenced by the type and amount of said catalyst, if used. By suitably selecting such factors, therefore, the unsaturated aldehyde can be obtained in the high yield. It is generally preferred to effect the reaction at the temperatures exceeding 100° C., preferably exceeding 130° C., particularly no lower than 150° C., for 1 minute to 50 hours, particulary from 5 minutes to 20 hours.

The reaction can be practiced either in vapor phase or liquid phase, while normally liquid phase is preferred. The liquid phase reaction, furthermore, is preferably practiced in the presence of solvent inert to the reaction. As the inert solvent, any of those mentioned in the foregoing section [I-1] can be used. The reaction can be practiced either batchwise or continuously.

Hereinafter the invention will be more specifically explained with reference to the following working Examples, with the understanding that the scope of this invention is in no way thereby limited. In the Examples, the parts are by weight unless otherwise sepcified. Also of the given analyses data, the infrared absorption spectrum was measured with Shimazu IR-27-G diffraction grating type device, using KBr plate as the cell. The NMR data were obtained by the test with Nippon Denshi GNM-MH-100 (100 MHz), using $CCl_4$ solvent.

The molecular weight and elementary analysis values were determined by Nippon Denshi JMS-D-100 high resolving power mass spectrometer. The quantitative analysis of the result of each reaction was effected by means of gas chromatography. The instrument employed was Yanagimoto G-80 Model gas chromatogram, the column being mainly the 2-m. glass column packed with OV-17–0.5% glass beads carrier.

EXAMPLE 1

84 parts of 3-methyl-3-butenal-1, 148 parts of ethyl o-formate, 100 parts of absolute ethanol, and 2 parts of ammonium nitrate were reacted for 6 hours at room temperature under stirring, and thereafter the reaction system was transferred into a distillation flask containing 5 parts of sodium carbonate, to be vacuum-distilled. Thus 120 parts of 3-methyl-3-butenal diethylacetal boiling at 154°–155° C. was obtained.

50 parts of thus obtained 3-methyl-3-butenal-1-diethylacetal, 70 parts of pulenol, 150 parts of toluene, and 2 parts of ammonium sulfate were charged in a flask equipped with a distillation column, thermometer and nitrogen gas inlet tube, and heated to boiling. Thus the ethanol and toluene were distilled off from the top of the distillation column. The heating was stopped when the temperature at the column top reached the boiling point of toluene, and the reaction product was transferred into a distillation flask containing 4 parts of sodium carbonate, and distilled in vacuo.

Results of the distillation:

The first reaction was identified to be 1-ethoxy-1-(3-methyl-2-butenyloxy)-3-methyl-3-butene, and the second fraction, 1,1-di-(3-methyl-2-butenyloxy)-3-methyl-3-butene. The analysis results of the first and second fractions were as shown in Tables A and B respectively.

Table A

| Run No. 1 | | Acetal | | | | unsaturated carbonyl compound | | |
|---|---|---|---|---|---|---|---|---|
| Structure | | CH₂=C(CH₃)—CH₂—CH(O—CH₂—CH₃)(O—CH₂—CH=C(CH₃)—CH₃) [I] (c) (b) (a) (d) (e) | | | | CH₃—C(CH₃)=CH—CH₂—CH₂—C(CH₃)=CH—CHO [II] | | |
| | | 1-ethoxy-1-(3-methyl-2-butenyloxy)-3- C₁₂H₂₂O | | | | 3,7-dimethyl-2,6-octadienal C₁₀H₁₆O | | |
| B.P. °C./mmHg | | 89.90/3 | | | | 117-9/20 | | |
| High-mass data | Calculated | C₁₂H₂₂O₂ | 182.1670 | | | C₁₀H₁₆O | 152.1201 | |
| | Found | C₁₂H₂₂O₂ | 182.1655 | | | C₁₀H₁₆O | 152.1182 | |
| IR spectrum (specific absorption) | | νC=C | 1675, 1650 | | | C=C—CHO | | |
| | | νC—O—C | 1113, 1053 | | | νC=O | 1670 | |
| | | C—C=CH₂ δCH | 887 | | | C=C νC=C | 1630 | |
| | | | τ value | H number | | | τ value | H number |
| NMR spectrum (specific absorption) | | H(a) | 5.39–5.50(t) | 1 | | H(a) | 0.08–0.26(t) | 1 |
| | | H(b) | 7.71–7.77(d) | 2 | | H(b) | 4.26(d) | 1 |
| | | H(c) | 5.26(s) | 2 | | H(c) | 4.84–5.04(m) | 1 |
| | | H(d) | 6.00–6.07(d) | 2 | | | | |
| | | H(e) | 4.66–4.80(t) | 1 | | | | |

Table B

| Run No. 2 | | Acetal | | | | unsaturated carbonyl compound | | |
|---|---|---|---|---|---|---|---|---|
| Structure | | CH₂=C(CH₃)—CH₂—CH(O—CH₂—CH=C(CH₃)—CH₃)(O—CH₂—CH=C(CH₃)—CH₃) [I] (c) (b) (a) (d) (e) | | | | CH₃—C(CH₃)=CH—CH₂—CH₂—C(CH₃)=CH—CHO [II] (c) (b) (a) | | |
| | | 1,1-di-(3-methyl-2-butenyloxy)-3-methyl-3-butene C₁₅H₂₆O₂ | | | | 3,7-dimethyl-2,6-octadienal C₁₀H₁₆O | | |
| B.P. °C./mmHg | | 89/0.5 | | | | 117-9/20 | | |
| High-mass data | Calculated | C₁₅H₂₆O₂ | 238.1935 | | | C₁₀H₁₆O | 152.1201 | |
| | Found | C₁₅H₂₆O₂ | 238.1949 | | | C₁₀H₁₆O | 152.1182 | |
| IR spectrum (specific absorption) | | ν C=C | 1675, 1650 | | | C=C—CHO | | |
| | | ν C—O—C | 1105, 1075, 1050, 1015 | | | ν C=O | 1670 | |
| | | —C=CH₂ δCH | 885 | | | C=C νC=C | 1630 | |
| | | | τ value | H number | | | τ value | H number |
| NMR spectrum (specific absorption) | | H(a) | 5.36–5.48(t) | 1 | | H(a) | 0.08–0.26(t) | 1 |
| | | H(b) | 7.70–7.76(d) | 2 | | | | |
| | | H(c) | 5.26(s) | 2 | | H(b) | 4.26(d) | 1 |
| | | H(d) | 6.00–6.07(d) | 4 | | H(c) | 4.84–5.04(m) | 1 |
| | | H(e) | 4.66–4.80(t) | 2 | | | | |

Thus,

| first fraction 89–90° C./3 mmHg | 34 parts |
|---|---|
| second fraction 89° C./0.5 mmHg | 21 parts | were obtained.

Results of IR spectrum, NMR, and mass spectrum analysis:

EXAMPLES 2-19

The 1,1-di-(3-methyl-2-butenyloxy)-3-methyl-3-butene (3-methyl-3-butenal-1-dipulenylacetal) synthesized in Example 1 was packed in a sealed tube, and reacted under various conditions, in all cases forming 3,7-dimethyl-2,6-octadienal (citral). The results were as shown in Table 1.

The result of analyzing the 3,7-dimethyl-2,6-octadienal is shown also in Table B.

Table 1

| Example No. | Acetal (part) | Catalyst (mol %) | Solvent (part) | Temperature (°C.) | Time (min) | Acetal conversion (%) | Carbonyl compound obtained selectivity (%) |
|---|---|---|---|---|---|---|---|
| 2 | 0.1 | — | p-Xylene 1.72 | 150 | 3840 | 30.0 | 71.3 |
| 3 | 0.1 | methane sulfonic acid 0.01 | benzene 0.74 | 200 | 5 | 55.6 | 84.0 |
| 4 | 0.1 | methane sulfonic acid 0.01 | benzene 1.74 | 250 | 5 | 100 | 91.0 |
| 5 | 0.1 | methane sulfonic acid 0.01 | benzene 1.74 | 300 | 5 | 100 | 70.2 |
| 6 | 0.1 | p-toluene sulfonic acid 0.005 | benzene 1.74 | 240 | 5 | 100 | 89.7 |
| 7 | 0.1 | oxalic acid 0.5 | benzene 1.74 | 250 | 30 | 87.0 | 70.6 |
| 8 | 0.05 | sulfuric acid 0.02 | benzene 0.87 | 270 | 3 | 100 | 77.2 |
| 9 | 0.1 | isophthalic acid 200 | benzene 1.74 | 200 | 30 | 56.3 | 88.8 |
| 10 | 0.1 | benzoic acid 100 | benzene 1.74 | 200 | 30 | 88.6 | 85.8 |
| 11 | 0.1 | — | 1.74 | 250 | 30 | 72.3 | 76.1 |
| 12 | 0.1 | p-toluene sulfonic acid 0.005 | n-heptane 2 | 230 | 5 | 34.5 | 93.6 |
| 13 | 0.1 | p-toluene sulfonic acid 0.005 | chrodo benzene 2 | 200 | 5 | 79.8 | 91.0 |
| 14 | 0.1 | p-toluene sulfonic acid 0.005 | tetra-hydro-furane 2 | 230 | 5 | 47.2 | 88.1 |
| 15 | 0.1 | p-toluene sulfonic acid 0.005 | cyclohexane 2 | 300 | 5 | 92.6 | 73.9 |
| 16 | 0.1 | — | ethylacetate 2 | 250 | 30 | 81.8 | 70.3 |
| 17 | 0.1 | — | p-xylene 2 | 250 | 30 | 93.8 | 68.2 |
| 18 | 0.1 | methane sulfonic acid 0.01 | — | 250 | 5 | 22.5 | 51.1 |
| 19 | 0.1 | — | — | 250 | 30 | 100 | 19.8 |

EXAMPLES 20–38

The alcohol-exchange reaction was effected between various combinations of β,γ-aldehyde-ethylacetal and allyl alcohol, similarly to Example 1, to synthesize various acetals shown in Table 2. The analyses values of thus obtained acetals, as well as those of α,β-unsaturated aldehydes obtained upon thermally decomposing and rearranging the acetals under various conditions, were as shown in Tables C through P.

Also the conditions of thermal decomposition of those acetals are given in Table 3, together with the results of the decomposition.

In Table 3, the marks attached to the acetals and formed α,β-unsaturated aldehydes correspond to those of the compounds in Tables C through P.

Table 2

| Example No. | Acetal fed | Allylalcohol | Result |
|---|---|---|---|
| 20–23 | 3-methyl-3-butenal diethyl acetal | prenyl alcohol | Table A |
| 24 | 3-methyl-3-butenal diethyl acetal | allyl alcohol | Table C |
| 25 | 3-methyl-3-butenal diethyl acetal | methallyl alcohol | Table D |
| 26 | 3-methyl-3-butenal diethyl acetal | crotonyl alcohol | Table E |
| 27 | 3-methyl-3-butenal diethyl acetal | gelanyl alcohol prenyl alcohol | Table F |
| 28, 29 | 3-methyl-3-butenal diethyl acetal | geranyl alcohol | Table G |
| 30 | 3-methyl-3-butenal diethyl acetal | farnesol | Table H |
| 31 | 3-methyl-3-butenal diethyl acetal | phytol | Table I |
| 32 | 3-methyl-3-butenal diethyl acetal | cyclogelanyl alcohol | Table J |
| 33 | 3-methyl-3-butenal diethyl acetal | furfuryl alcohol | Table K |
| 34 | 3-methyl-3-butenal diethyl acetal | 2-methyl-2-butanol | Table L |
| 35 | 3-methyl-3-butenal diethyl acetal | 1-methyl-2-propenol | Table M |
| 36 | 3-butenal-diethyl acetal | prenyl alcohol | Table N |
| 37 | 2-methyl-3-butenal-diethyl acetal | methallyl alcohol | Table O |
| 38 | 3-octenal dimethyl acetal | prenyl alcohol | Table P |

Table C

| Run No. 3 | Acetal | | unsaturated carbonyl compound | |
|---|---|---|---|---|
| Structure | $\underset{(c)}{CH_2}=\underset{}{\overset{CH_3}{\underset{|}{C}}}-\underset{(b)}{CH_2}-\underset{(a)}{CH}\underset{\diagdown}{\diagup}\underset{(d)\ (e)\ (f)}{\overset{OCH_2CH=CH_2}{OCH_2-CH=CH_2}}$ [I] | | $\underset{(d)}{CH_2}-\underset{(c)}{CH}-CH_2-CH_2-\overset{CH_3}{\underset{|}{C}}=\underset{(b)}{CH}-\underset{(a)}{CHO}$ [II] | |
| | 1,1-di-(3-propenyloxy)-3-methyl-3-butene | | 3-methyl-2,6-heptadienal | |
| | $C_{11}H_{18}O_2$ | | $C_8H_{12}O$ | |
| B.P. °C./mmHg | 53–54/1 | | 79°/13 | |
| High-mass data Calculated | $C_{11}H_{18}O_2$ | 182.1303 | $C_8H_{12}O$ | 124.0887 |
| High-mass data Found | $C_{11}H_{18}O_2$ | 182.1284 | $C_8H_{12}O$ | 124.0834 |
| IR spectrum (specific absorption) | $\nu C=C$ | 1650 | $C=C-CHO$ | |
| | $\nu C-O-C$ | 1115, 1050, 1030 | $\nu C=O$ | 1675 |
| | | 920, 890 | $\nu C=C$ | 1640 |
| | $-\overset{|}{C}=CH_2$ $\delta CH$ | | $\delta CH$ | 913 |
| | | τ value | H number | | τ value | H number |
| NMR spectrum (specific absorption) | H(a) | 5.30–5.40(t) | 1 | H(a) | 0.25(d) | 1 |
| | H(b) | 7.70(d) | 2 | H(b)(c) | 4.12–4.38(m) | 2 |
| | H(c) | 5.25(s) | 2 | H(d) | 4.92–5.14(m) | 2 |
| | H(d) | 6.02(d) | 4 | | | |
| | H(e) | 3.98–4.39(m) | 2 | | | |
| | H(f) | 4.71–4.96(t) | 4 | | | |

Table D

| Run No. 4 | Acetal | | unsaturated carbonyl compound | |
|---|---|---|---|---|
| Structure | $\underset{(c)}{CH_2}=\overset{CH_3}{\underset{|}{C}}-\underset{(b)}{CH_2}-\underset{(a)}{CH}\underset{\diagdown}{\diagup}\underset{(d)}{\overset{O-CH_2-\overset{CH_3}{\underset{|}{C}}=CH_2}{O-CH_2-\underset{|}{C}=CH_2}}\ _{CH_3(e)}$ [I] | | $\underset{(c)}{CH_2}=\overset{CH_3}{\underset{|}{C}}-CH_2-CH_2-\overset{CH_3}{\underset{|}{C}}=\underset{(b)}{CH}-\underset{(a)}{CHO}$ [II] | |
| | 1,1-di-(2-methyl-2-propenyloxy)-methyl-3-butene | | 3,6-dimethyl-2,6-heptadienal | |
| | $C_{13}H_{22}O_2$ | | $C_9H_{14}O$ | |
| B.P. °C./mmHg | 70/0.55 | | 70/3.5 | |
| High-mass data Calculated | $C_{13}H_{22}O_2$ | 210.1619 | $C_9H_{14}O$ | 138.1044 |
| High-mass data Found | $C_{13}H_{22}O_2$ | 210.1572 | $C_9H_{14}O$ | 138.1009 |
| IR spectrum | $\nu C=C$ | 1650 | $C=C-CHO\,\nu C=O$ | 1672 |
| | $\nu C-O-C$ | 1120, 1080, 1060, 1022 | | 885 |
| (specific absorption) | | 890 | $-\overset{|}{C}=CH_2\,\delta CH$ | |
| | $-\overset{|}{C}=CH_2$ $\delta CH$ | | | |
| | | τ value | H number | | τ value | H number |
| NMR spectrum (specific absorption) | H(a) | 5.29–5.40(t) | 1 | H(a) | 0.09–0.23(t) | 1 |
| | H(b) | 7.66(d) | 2 | H(b) | 4.22(d) | 1 |
| | H(c) | 5.18(s) | 2 | H(c) | 4.28(s) | 2 |
| | H(d) | 6.08(s) | 4 | | | |
| | H(e) | 5.14(d) | 4 | | | |

Table E

| Run No. 5 | Acetal | | unsaturated carbonyl compound | |
|---|---|---|---|---|
| Structure | $\underset{(c)}{CH_2}=\overset{CH_3}{\underset{|}{C}}-\underset{(b)}{CH_2}-\underset{(a)}{CH}\underset{\diagdown}{\diagup}\underset{(d)\ (e)\ (f)}{\overset{O-CH_2-CH=CH-CH_3}{O-CH_2-CH=CH-CH_3}}$ [I] | | $CH_3-\underset{(d)}{CH}=\underset{(c)}{CH}-CH_2-CH_2-\overset{CH_3}{\underset{|}{C}}=\underset{(b)}{CH}-\underset{(a)}{CHO}$ [II] | |
| | 1,1-di-(2-butenyloxy)-3-methyl-3-butene | | 3-methyl-2,6-octadienal | |
| | $C_{13}H_{22}O_2$ | | $C_9H_{14}O$ | |
| B.P. °C./mmHg | 80°/0.2 | | 66/3 | |
| High-mass data Calculated | $C_{13}H_{22}O_2$ | 210.1621 | $C_9H_{14}O$ | 138.1046 |
| High-mass data Found | $C_{13}H_{22}O_2$ | 210.1622 | $C_9H_{14}O$ | 138.1066 |

Table E-continued

| Run No. 5 | Acetal | | | unsaturated carbonyl compound | | |
|---|---|---|---|---|---|---|
| IR spectrum (specific absorption) | $\nu C=C$<br>$\nu C-O-C$<br>$\underset{\delta CH}{-\overset{\|}{C}=CH_2}$ | 1650<br>1114, 1070, 1050, 1024<br>890 | | $\nu C=O$<br>$\nu C=C$ | 1670<br>1630 | |
| | | τ value | H number | | τ value | H number |
| NMR spectrum (specific absorption) | H(a)<br>H(b)<br>H(c)<br>H(d)<br>H(e,f) | 5.36–5.58(t)<br>7.73(d)<br>5.27(s)<br>5.96–6.16(m)<br>4.37–4.56(m) | 1<br>2<br>2<br>4<br>2 | H(a)<br>H(b)<br>H(c,d) | 0.20(d)<br>4.24(d)<br>4.52–4.64 | 1<br>1<br>2 |

Table F

Run No. 6

[I] acetal

Structure:

$$CH_2=C(CH_3)-CH_2-CH(a)(O-CH_2-CH=C(CH_3)-CH_3\ (d)(e)(f))_2$$ (b)(c)

1-(3-methyl-2-butenyoxy)-1-(3,7-dimethyl-2,6-octadienyloxy)-3-methyl-3-butene

| | |
|---|---|
| B.P. °C./mmHg | 122.5/0.2 |
| High-mass data Calculated | $C_{20}H_{34}O_2$ 306.2556 |
| Found | $C_{20}H_{34}O_2$ 306.2508 |
| IR spectrum (specific absorption) | $\nu C=C$ 1670, 1648 <br> $\nu C-O-C$ 1108, 1064, 1050, 1018 <br> $-C=CH_2$ 886 <br> $\delta CH$ |
| NMR spectrum (specific absorption) | $\nu C=C$ <br> $\tau$ value / H number <br> H(a) 5.38–5.50(t) / 1 <br> H(b) 7.72–7.77(d) / 2 <br> H(c) 5.28(s) / 2 <br> H(d) 6.00–6.07 / 2 <br> H(e) 4.68–4.80(t) / 2 <br> H(f) 4.88–5.02(t) / 1 |

[II] unsaturated carbonyl compound

Structure:

$$CH_3-C(CH_3)=CH-CH_2-CH_2-C(CH_3)=CH-CHO$$

3,7-dimethyl-2,6-octadienal

| | |
|---|---|
| | $C_{10}H_{16}O$ <br> 117–9/20 |
| | $C_{10}H_{16}O$ 152.1201 |
| | 152.1182 |
| $\nu C=C-CHO$, $\nu C=O$, $\nu C=C$ | 1670 |
| | 1630 |
| H(a) | $\tau$ value / H number <br> 0.08–0.26(t) / 1 |
| H(b) | 4.26(d) / 1 |
| H(c) | 4.84–5.04(m) / 1 |

[III] unsaturated carbonyl compound

Structure:

$$CH_3-C(CH_3)=CH-CH_2-CH_2-C(CH_3)=CH-CH_2-CH_2-C(CH_3)=CH-CHO$$
(d)            (c)            (b) (a)

3,7,11-trimethyl-2,6,10-dodecatrienal

| | |
|---|---|
| B.P. °C./mmHg | 172–4/14 |
| High-mass data Calculated | $C_{15}H_{24}O$ 220.1828 |
| Found | $C_{15}H_{24}O$ 220.1820 |
| IR spectrum (specific absorption) | $\nu CO$ <br> $C=C-CHO$ 1676 <br> $C=C$ <br> $\nu C=C$ 1628 |
| NMR spectrum (specific absorption) | $\tau$ value / H number <br> H(a) 0.11, –0.26(t) / 1 <br> H(b) 4.25(d) / 1 <br> H(c,d) 4.84, –5.08(m) / 2 |

Table G

| Run No. 7 | acetal | unsaturated carbonyl compound |
|---|---|---|
| Structure | $CH_2=C(CH_3)-CH_2-CH$ (a) with two (b) $O-CH_2-CH=C(CH_3)-CH_2-CH_2-CH=C(CH_3)-CH_3$ (d)(e) groups (f); 1,1-di-(3,7-dimethyl-2,6-octadienyloxy)-3-methyl-3-butene | $CH_3-C(CH_3)=CH-CH_2-CH_2-C(CH_3)=CH-CH_2-CH_2-C(CH_3)=CH-CHO$ (c)(d)(b)(a); 3,7,11-trimethyl-2,6,10-dodecatrienal |
| | $C_{25}H_{42}O_2$ | $C_{15}H_{24}O$ |
| B.P. °C/mmHg | 165–169/0.18 | 172–4/14 |
| High-mass data Calculated | $C_{25}H_{42}O_2$ 374.3183 | $C_{15}H_{24}O$ 220.1828 |
| Found | 374.3179 | 220.1820 |
| IR spectrum (specific absorption) | $\nu C=C$ 1670, 1645; $\nu C-O=C$ 1108, 1070, 1050, 1020; $-C=CH_2$ 886; $\delta CH$ | $C=C-CHO$; $\nu CO$ 1676; $C=C$ 1628; $\nu C=C$ |
| NMR spectrum (specific absorption) | τ value; H(a) 5.35–5.46(t) H number 1; H(b) 7.71(d) 2; H(c) 5.24(s) 2; H(d) 6.00(d) 4; H(e) 4.64–4.77(t) 2; H(f) 4.86–5.00(m) | τ value; H(a) 0.11–0.26(t) H number 1; H(b) 4.25(d) 1; H(c,d) 4.84–5.08(m) 2 |

(II)

Table H

| Run No. 8 | acetal | | unsaturated carbonyl compound | |
|---|---|---|---|---|
| Structure | $CH_2=C(CH_3)-CH_2-CH(a)$ (c) (b) with $O-CH_2-CH=C(CH_3)-CH_2+CH_2-CH=C(CH_3)-CH_2\}_2H$ (d) (e) (f,g)<br>1,1-di-(3,7,11-trimethyl-2,6,10-dodecatrienyloxy)-3-methyl-3-butene<br>$C_{35}H_{58}O_2$<br>225–235/0.2 | (I) | $CH_3-C(CH_3)=CH-CH_2-CH_2-C(CH_3)=CH-CH_2-CH_2-C(CH_3)=CH-CH_2-CH_2-C(CH_3)=C-CHO$ (b) (a)<br>3,7,11,15-tetramethyl-2,6,10,14-hexadecatetraenal<br>$C_{20}H_{32}O$<br>155–156/3 | (II) |
| B.P. °C./mmHg | | | | |
| High-mass data Calculated | $C_{35}H_{58}O_2$ 510.4437 | | $C_{20}H_{32}O$ 288.2456 | |
| Found | $C_{35}H_{58}O_2$ 510.4442 | | $C_{20}H_{32}O$ 288.2524 | |
| IR spectrum (specific absorption) | $\nu C=C$ 1665, 1650<br>$\nu C-O-C$ 1110, 1075, 1050, 1020<br>$-C=CH_2$ $\delta$ CH 887 | | $C=C-CHO$<br>$\nu C=O$ 1675<br>$\nu C=C$<br>$\nu C=C$ 1630 | |
| NMR spectrum (specific absorption) | | H number | | H number |
| | | τ value | | τ value |
| | H(a) 5.35–5.46(t) | 1 | H(a) 0.14(d) | 1 |
| | H(b) 7.72(d) | 2 | H(b) 4.24(d) | 1 |
| | H(c) 5.25(s) | 2 | | |
| | H(d) 6.01(s) | 4 | | |
| | H(e) 4.65–4.72(t) | 2 | | |
| | H(f,g) 4.84–5.00(m) | 4 | | |

Table I

| Run No. 9 | acetal | | unsaturated carbonyl compound |
|---|---|---|---|
| Structure | $CH_2=C-CH_2-CH$ with $CH_3$ group (c), (b), (a), and branches $O-CH_2-CH=C-CH_2\text{-}(CH_2-CH_2-CH-CH_2)_3H$ with $CH_3$ groups (d), (e) [I] <br> 1,1-di-{(3,7,11,15-tetramethyl-2-hexade-cenyloxy)}-3-methyl-3-butene <br> $C_{45}H_{86}O_2$ <br> 230°/0.002 | → | $H\text{-}(CH_2-CH-CH_2-CH_2-CH_2)_3CH_2-C=$ with $CH_3$ groups, $CH-CH_2-CH_2-C=CH-CHO$ (c), (b), (a) [II] <br> 3,7,11,15,19-pentamethyl-2,6-eicosadienal <br> $C_{25}H_{46}O$ <br> 182–185/0.3 |
| B.P. °C./mmHg | | | |
| High-mass data — Calculated | $C_{45}H_{86}O_2$ 658.6635 | | $C_{25}H_{46}O$ 362.3190 |
| Found | $C_{45}H_{86}O_2$ 658.6615 | | $C_{25}H_{46}O$ 362.3222 |
| IR spectrum (specific absorption) | $\nu C\equiv C$ 1670, 1650 <br> 888 <br> $-C=CH_2$ <br> $\delta CH$ <br> $\nu C-O-C$ 1113, 1050, 1030 | | $C=C-CHO$ 1677 <br> $\nu C=C$ 1631 |
| NMR spectrum (specific absorption) | τ value <br> H(a) 5.38–5.50(t)    H number: 1 <br> H(b) 7.74(d)    2 <br> H(c) 5.27(s)    2 <br> H(d) 6.04(d)    4 <br> H(e) 4.68–4.82(t)    2 | | τ value <br> H(a) 0.13–0.28(t)    H number: 1 <br> H(b) 4.24(d)    1 <br> H(c) 4.91–5.01(m)    1 |

Table J

| Run No. 10 | acetal | | unsaturated carbonyl compound | |
|---|---|---|---|---|
| Structure | 1,1-di-(2,6,6-trimethyl-1-cyclohexene-1-methyleneoxy)-3-methyl-3-butene $C_{25}H_{42}O_2$ | [I] | β-dihydroionylidene acetoaldehyde $C_{15}H_{24}O$ | [II] |
| B.P. °C./mmHg | 170–171/0.2 | | 98°/0.1 | |
| High-mass data Calculated | $C_{25}H_{42}O_2$ | 374.3188 | $C_{15}H_{24}O$ | 220.1829 |
| Found | $C_{25}H_{42}O_2$ | 374.3245 | $C_{15}H_{24}O$ | 220.1855 |
| IR spectrum (specific absorption) | $\nu C=C$ | 1650 | C=C—CHO | |
| | $\nu C-O-C$ | 1108, 1065, 1045, 1013 | $\nu C=O$ | 1675 |
| | $\underset{\delta CH}{\overset{\mid}{C-C=CH_2}}$ | 885 | C=C $\nu C=C$ | 1630 |

| | | τ value | H number | | τ value | H number |
|---|---|---|---|---|---|---|
| NMR spectrum (specific absorption) | H(a) | 5.44–5.56(t) | 1 | H(a) | 0.10(d) | 1 |
| | H(b) | 7.68 (d) | 2 | H(b) | 4.19(d) | 1 |
| | H(c) | 5.26 (s) | 2 | | | |
| | H(d) | 5.84–6.22(a) | 4 | | | |

Table K

| Run No. 11 | acetal | | unsaturated carbonyl compound | |
|---|---|---|---|---|
| Structure | 1,1-di-(2-furfuryloxy)-3-methyl-3-butene $C_{15}H_{18}O_4$ | [I] | 5-(2-furyl)-3-methyl-2-pentanal $C_{10}H_{12}O_2$ | [II] |
| B.P. °C./mmHg | 111–112/0.2 | | 75°/0.25 | |
| High-mass data Calculated | $C_{15}H_{18}O_4$ | 262.1204 | $C_{10}H_{12}O$ | 164.0837 |
| Found | $C_{15}H_{18}O_4$ | 262.1172 | $C_{10}H_{12}O_2$ | 164.0830 |
| IR spectrum (specific absorption) | $\nu C=C$ | 1650 | C=C—CHO | |
| | $\nu C-O-C$ | 1110, 1070, 1040, 1010 | $\nu CO$ | 1672 |
| | | 890 | | 1507, 883, 732 |
| | $-\overset{\mid}{C}=CH_2 \delta CH$ | 1503, 883, 735 | | |

| | | τ value | H number | | τ value | H number |
|---|---|---|---|---|---|---|
| NMR spectrum (specific absorption) | H(a,c) | 5.20–5.32(m) | 3 | H(a) | 0.11–0.37(Q) | 1 |
| | H(b) | 7.67(d) | 2 | H(e) | 2.76(s) | 1 |
| | H(d) | 5.52(s) | 4 | H(d) | 3.81(d) | 1 |
| | H(e) | 2.76(s) | 2 | H(c) | 4.05(d) | 1 |
| | H(e,f) | 3.77(d) | 4 | H(b) | 4.23 | 1 |

Table L

Run No. 12

| | acetal [I] | | unsaturated carbonyl compound [II] | |
|---|---|---|---|---|

Structure (acetal [I]):

```
         CH3                    O—CH2—C=CH—CH3
          |                    /         |
CH2=C—CH2—CH                   (d)  (e)  CH3
 (c)  (b) (a)  \
                O—CH2—C=CH—CH3
                     |
                     CH3
```
1,1-di-(2-methyl-2-butenyloxy)-3-methyl-3-butene $C_{15}H_{26}O_2$ Structure (unsaturated carbonyl compound [II]):

```
         CH3              CH3
          |                |
CH3—CH=C—CH2—CH2—C=CH—CHO
       (c)           (b)   (a)
```
3,6-dimethyl-2,6-octadienal $C_{10}H_{16}O$

| | | | | |
|---|---|---|---|---|
| B.P. °C./mmHg | | 95–99/0.35 | | 61–62/0.15 |
| High- Calculated mass | $C_{15}H_{26}O_2$ | 238.1934 | $C_{10}H_{16}O$ | 152.1201 |
| data Found | $C_{15}H_{26}O_2$ | 238.1957 | $C_{10}H_{16}O$ | 152.1197 |
| IR spectrum (specific absorption) | $\nu$ C=C | 1678, 1650 | C=C—CHO | |
| | $\nu$ C—O—C | 1120, 1077, 1050, 1015 | $\nu$ C=O | 1678 |
| | $\nu$ C=C<br>$\|$<br>—C=CH₂ | | $\nu$ C=C | 1630 |
| | δ CH | 888 | | |

| | | τ value | H number | | τ value | H number |
|---|---|---|---|---|---|---|
| NMR spectrum (specific absorption) | H(a) | 5.40–5.51(t) | 1 | H(a) | 0.26(d) | 1 |
| | H(b) | 7.73(d) | 2 | H(b) | 4.26(d) | 1 |
| | H(c) | 5.27(s) | 2 | H(c) | 4.68–4.88(m) | 1 |
| | H(d) | 6.05–6.32(Q) | 4 | | | |

Table M

Run No. 13

| | acetal [I] | | unsaturated carbonyl compound [II] | |
|---|---|---|---|---|

Structure (acetal [I]):

```
                      CH3
         CH3           |
          |           O—CH—CH=CH2
CH2=C—CH2—CH          (d) (e) (f)
 (c)  (b) (a)  \
                O—CH—CH=CH2
                  |
                  CH3
```
1,1-di-(1-methyl-2-propenyloxy)-3-methyl-3-butene $C_{13}H_{22}O_2$ Structure (unsaturated carbonyl compound [II]):

```
        CH3       CH3
         |         |
CH2=CH—CH—CH2—C=CH—CHO
(d) (c)        (b)  (a)
```
3,5-dimethyl-2,6-heptadienal $C_9H_{14}O$

| | | | | |
|---|---|---|---|---|
| B.P. °C./mmHg | | 57–59/0.15 | | 62–63/4 |
| High- Calculated mass | $C_{13}H_{22}O_2$ | 210.1621 | $C_9H_{14}O$ | 138.1044 |
| data Found | $C_{13}H_{22}O_2$ | 210.1575 | $C_9H_{14}O$ | 138.1029 |
| IR spectrum (specific absorption) | $\nu$ C=C | 1650 | C=C—CHO | |
| | $\nu$ C—O—C | 1110, 1065, 1040, 1015 | $\nu$ C=O | 1675 |
| | | | $\nu$ C=C | 1645 |
| | $\|$<br>—C=CH₂<br>δ CH | 920, 890 | $\|$<br>—C=CH₂<br>δ CH | 912 |

| | | τ value | H number | | τ value | H number |
|---|---|---|---|---|---|---|
| NMR spectrum (specific absorption) | H(a) | 5.36–5.48(t) | 1 | H(a) | 0.15–0.30(t) | 1 |
| | H(b) | 7.77(d) | 2 | H(b,c) | 4.15–4.53(m) | 1 |
| | H(c) | 5.29(s) | 2 | H(d) | 4.97–5.13(t) | 1 |
| | H(d) | 5.82–610(m) | 2 | | | |
| | H(e) | 4.04–4.53(m) | 2 | | | |
| | H(f) | 4.81–5.05(m) | 4 | | | |

Table N

Run No. 14

| | acetal | unsaturated carbonyl compound |
|---|---|---|

Structure (acetal):

```
                         CH3
                          |
              O—CH2—CH=C—CH3
             /   (e)  (f)
H2C=CH—CH2—CH
(d) (c) (b) (a) \
                O—CH2—CH=C—CH3
                              |
                              CH3
```

Structure (unsaturated carbonyl compound):

```
      CH3
       |
CH3—C=CH—CH2—CH2—CH=CH—CHO
       (d)         (c)  (b)  (a)
```

Table N-continued

Run No. 14

| | acetal | | unsaturated carbonyl compound | |
|---|---|---|---|---|
| | 1,1-di-(3-methyl-2-butenyloxy)-3-butene- C$_{14}$H$_{24}$O$_2$ | | 7-methyl-2,6-octadienal C$_9$H$_{14}$O | |
| B.P. °C./mmHf | | 90/0.2 | | 64/3 |
| High-mass Calculated | C$_{14}$H$_{24}$O$_2$ | 224.1773 | C$_9$H$_{14}$O | 138.1047 |
| data Found | C$_{14}$H$_{24}$O$_2$ | 224.1755 | C$_9$H$_{14}$O | 138.1051 |
| IR spectrum (specific absorption) | $\nu$ C=C | 1678, 1645 | C=C—CHO $\nu$ C=O | 1692 |
| | —C=CH$_2$ | | | |
| | $\delta$ CH | 922 | $\nu$ C=C | 1635 |
| | | $\tau$ value / H number | | $\tau$ value / H number |
| NMR spectrum (specific absorption) | H(a) | 5.49–5.60(t) / 1 | H(a) | 0.63(d) / 1 |
| | H(b) | 7.62–7.75(t) / 2 | H(b) | 3.87–4.10(m) / 1 |
| | H(c) | 4.12–4.46(m) / 1 | H(c) | 3.12–3.40(m) / 1 |
| | H(d) | 4.87–5.04(t) / 2 | H(d) | 4.86–4.98(t) / 1 |
| | H(e) | 6.05(d) / 4 | | |
| | H(f) | 4.67–4.80(t) / 2 | | |

Table O

Run No. 15

| | acetal | | unsaturated carbonyl compound | |
|---|---|---|---|---|
| Structure | 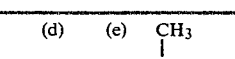 | | 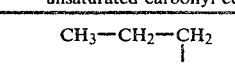 | |
| | 1,1-di-(2-methyl-2-propenyloxy)-2-methyl-3-butene C$_{13}$H$_{22}$O$_2$ | | 2,6-dimethyl-2,6-heptadienal C$_9$H$_{14}$O | |
| B.P. °C./mmHf | | 73–74/3 | | 61/4 |
| High-mass Calculated | C$_{13}$H$_{22}$O$_2$ | 210.1635 | C$_9$H$_{14}$O | 138.1045 |
| data Found | C$_{13}$H$_{22}$O$_2$ | 210.1667 | C$_9$H$_{14}$O | 138.1049 |
| IR spectrum (specific absorption) | $\nu$ C=C | 1660 | C=C—CHO | |
| | $\nu$ C—O—C | 1108, 1055, 1035 | $\nu$ C=O | 1690 |
| | | | $\nu$ C=C | 1650 |
| | —C=CH$_2$ | | | |
| | $\delta$ CH | 996 | —C=CH$_2$ | |
| | | | $\delta$ CH | 890 |
| | | $\tau$ value / H number | | $\tau$ value / H number |
| NMR spectrum (specific absorption) | H(a) | 5.78 (d) / 1 | H(a) | 0.74(s) and —0.2 (s) / 1 |
| | H(b) | 7.44–7.64 (Q) / 1 | H(b) | 3.53–3.71 (t) / 1 |
| | H(c) | 4.03–4.37 (m) / 1 | H(c) | 5.28 (d) / 1 |
| | H(d,f) | 4.92–5.20 (Q) / 6 | | |
| | H(e) | 5.99–6.26 (t) / 4 | | |

Table P

Run No. 16

| | acetal | | unsaturated carbonyl compound | |
|---|---|---|---|---|
| Structure | 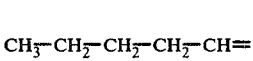 | | 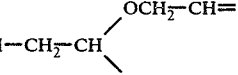 | |
| | 1,1-di(3-methyl-2-butenyloxy)-3-octene C$_{18}$H$_{32}$O$_2$ | | 7-methyl-5-butyl-2,6-octadienal C$_{13}$H$_{22}$O | |
| B.P. °C./mmHg | | 122/03 | | 79–81/0.7 |
| High-mass Calculated | C$_{18}$H$_{32}$O$_2$ | 280.2399 | C$_{13}$H$_{22}$O | 194.1671 |
| data Found | C$_{18}$H$_{32}$O$_2$ | 280.2340 | C$_{13}$H$_{22}$O | 194.1652 |
| IR spectrum (specific absorption) | $\nu$c=c | 1678 | C=C—CHO $\nu$C=O | 1690 |
| | $\nu$c—o—c | 1105, 1045, 1015 | $\nu$C=C | 1632 |

Table P-continued

Run No. 16

| | | acetal | | | | unsaturated carbonyl compound | |
|---|---|---|---|---|---|---|---|
| | | τvalue | H number | | | τvalue | H number |
| NMR spectrum (specific absorption) | H(a) | 5.56–5.64 (t) | 1 | | H(a) | 0.62 (d) | 1 |
| | H(b,c,e) | 4.57–4.81 (m) | 4 | | H(b) | 3.83–4.16 (Q) | 1 |
| | H(d) | 6.06 (d) | 4 | | H(c) | 3.37–3.60 (Q) | 1 |
| | | | | | H(d) | 4.90–5.04 (t) | 1 |

Table 3

| Example No. | Acetal (part) | Catalyst (mol %) | Solvent (part) | Temperature (°C.) | Time (min) | Acetal conversion | α,β-unsaturated aldehyde obtained Selectivity |
|---|---|---|---|---|---|---|---|
| 20 | 1-[I] 0.1 | — | benzene 1.74 | 25C | 30 | 1-[I] 93.0 | 1-[II] 56.0 |
| 21 | 1-[I] 0.1 | — | n-heptane 1.36 | 250 | 30 | 1-[I] 34.1 | 1-[II] 42.8 |
| 22 | 1-[I] 0.1 | — | | 250 | 30 | 1-[I] 98.3 | 1-[II] 22.0 |
| 23 | 1-[I] 0.1 | methane suflonic acid 0.01 | benzene 1.74 | 230 | 10 | 1-[I] 86.6 | 1-[II] 74.2 |
| 24 | 3-[I] 0.1 | methane sulfonic acid 0.2 | benzene 1.74 | 250 | 5 | 3-[I] 100 | 3-[II] 90.1 |
| 25 | 4-[I] 0.1 | methane sulfonic acid 0.2 | benzene 1.74 | 250 | 5 | 4-[I] 84.2 | 4-[II] 75.5 |
| 26 | 5-[I] 0.05 | methane sulfonic acid 0.2 | benzene 0.87 | 250 | 5 | 5-[I] 100 | 5-[II] 92.6 |
| 27 | 6-[I] 0.1 | methane sulfonic acid 0.01 | benzene 1.74 | 250 | 5 | 6-[I] 100 | 6-[II] 46.5  6-[III] 41.5 |
| 28 | 7-[I] 0.1 | oxalic acid 0.5 | benzene 1.74 | 250 | 30 | 7-[I] 95.5 | 7-[II] 76.5 |
| 29 | 7-[I] 0.1 | methane sulfonic acid 0.01 | benzene 1.74 | 260 | 5 | 98.7 | 92.7 |
| 30 | 8-[I] 0.05 | methane sulfonic acid 0.01 | benzene 0.87 | 250 | 15 | 8-[I] 100 | 8-[II] 70.2 |
| 31 | 9-[I] 0.05 | methane sulfonic acid 0.01 | benzene 0.87 | 250 | 15 | 9-[I] 100 | 9-[II] 61.4 |
| 32 | 10-[I] 0.1 | methane sulfonic acid 0.1 | benzene 1.74 | 250 | 5 | 10-[I] 100 | 10-[II] 75.4 |
| 33 | 11-[I] 0.05 | methane sulfonic acid 0.2 | benzene 0.87 | 250 | 5 | 11-[I] ≈100 | 11-[II] ≈100 |
| 34 | 12-[I] 0.05 | methane sulfonic acid 0.1 | benzene 0.87 | 250 | 5 | 12-[I] 95.1 | 12-[II] 81.3 |
| 35 | 13-[I] 0.05 | methane sulfonic acid 0.1 | benzene 0.87 | 280 | 5 | 13-[I] 100 | 13-[II] 64.8 |
| 36 | 14-[I] 0.05 | methane sulfonic acid 0.1 | benzene 0.87 | 250 | 5 | 14-[I] 100 | 14-[II] 73.8 |
| 37 | 15-[I] 0.05 | methane sulfonic acid 0.1 | benzene 0.87 | 250 | 10 | 15-[I] 100 | 15-[II] 87.7 |
| 28 | 16-[I] 0.05 | methane sulfonic acid 0.1 | benzene 0.87 | 250 | 5 | 16-[I] 10 | 16-[II] 85.5 |

EXAMPLES 39–44

3-Methyl-3-butenal-1, pulenol, and the catalyst were charged in a sealed tube, and reacted under various conditions. The reaction product of each run was analyzed by means of gas chromatography, with the results as shown in Table 4, in which the aldehyde is 3-methylbutenal-1, POH stands for pulenol, and CT, citral as the object product.

Table 4

| Example No. | Aldehyde (part) | POH (part) | Solvent (part) | Catalyst (mol %) | Temperature (°C.) | Reaction time (min) | Aldehyde conversion (%) | CT Selectivity (%) |
|---|---|---|---|---|---|---|---|---|
| 39 | 0.1 | 0.21 | — | — | 250 | 120 | 100 | 10.8 |
| 40 | 0.1 | 0.21 | chrolobenzene 2 | methane sulfonic acid | 250 | 120 | 89.9 | 15.5 |
| 41 | 0.1 | 0.7 | — | 0.005 | 220 | 120 | 100 | 20.9 |
| 42 | 0.1 | 0.7 | — | oxalic acid 0.5 | 220 | 120 | 100 | 22.6 |
| 43 | 0.1 | 0.7 | — | benzoic acid 5.0 | 220 | 120 | 100 | 18.7 |

Table 4-continued

| Example No. | Aldehyde (part) | POH (part) | Solvent (part) | Catalyst (mol %) | Temperature (°C.) | Reaction time (min) | Aldehyde conversion (%) | CT Selectivity (%) |
|---|---|---|---|---|---|---|---|---|
| 44 | 0.1 | 0.7 | n-hepthane 2 | oxalic acid 0.5 | 220 | 120 | 92.9 | 15.0 |

EXAMPLES 45–51

3-Methyl-3-butenal-diethylacetal was reacted with pulenol in a sealed tube with the following results shown in Table 5.

In the Table 5, "acetal" stands for 3-methyl-3-butenal-1-diethyl acetal, and "CT", for citral. The "CT selectivity" is mol % of the formed citral to the converted acetal.

Table 5

| Example No. | Acetal (part) | Pulenol (part) | Solvent (part) | Catalyst (mol %) | Temperature (°C.) | Reaction time (min) | Acetal conversion (%) | CT selectivity (%) |
|---|---|---|---|---|---|---|---|---|
| 45 | 0.1 | 0.5 | — | — | 230 | 120 | 97.7 | 21.3 |
| 46 | 0.1 | 0.5 | benzene 2 | — | 250 | 120 | 80.4 | 26.7 |
| 47 | 0.1 | 0.5 | iso-propyl-ether 2 | — | 250 | 120 | 57.1 | 22.6 |
| 48 | 0.1 | 0.5 | benzene 2 | methane sulfonic acid 0.005 | 250 | 60 | 88.0 | 23.9 |
| 49 | 0.1 | 0.5 | benzene 2 | p-toluene sulfonic acid 0.005 | 250 | 60 | 100 | 33.6 |
| 50 | 0.1 | 0.5 | benzene 2 | oxalic acid 0.5 | 250 | 60 | 100 | 30.8 |
| 51 | 0.1 | 0.5 | benzene 2 | benzoic acid 1.0 | 250 | 60 | 49.0 | 19.6 |

EXAMPLE 52

0.05 part of 1,1-di-(pentyloxy)-3-methyl-3-butene which was an alcohol-exchange product of 1,1-diethoxy-3-methyl-3-butene and n-pental and had a boiling point of 86° C. at 0.4 mmHg was charged in a sealed tube together with 0.1 part of prenyl alcohol and 0.5 mol % of oxalic acid and the mixture was reacted at 250° C. for 60 minutes. The reaction mixture was analyzed by gas chromatography with the following results;

| | |
|---|---|
| Conversion of 1,1-di(pentyloxy)-3-methyl-3-butene | 100% |
| Selectivity of 3,7-dimethyl-2,6-octadienal (citral) | 33.2% |

EXAMPLE 53

2.5 parts of 3-methyl-3-butenal-1, 15 parts of pulenol, 0.1 part of ammonium sulfate, and 25 vol. parts of benzene were charged in a rotatory band rectification column comprising the reaction zone of 100 vol. parts. The system was reacted at 95° C. for 2 hours, the volume thereof being maintained constant by feeding thereinto fresh benzene at a rate of 10 vol. parts per hour and distilling the water-containing benzene off at a rate of 10 vol. parts per hour. Whereupon 100% of the 3-methyl-3-butenal-1 was converted, and 3-methyl-3-butenal-1-dipulenylacetal was obtained with the selectivity of 99%. To the reaction liquid an equimolar amount to the ammonium sulfate of sodium carbonate was added, and then 1 mol % to the initially charged 3-methyl-3-butenal-1 of isophthalic acid was added. The system was reacted for 5 minutes then at 250° C. Thus 80 mol % of the acetal was converted, and citral as the reaction product was formed in the yield of 49 mol % to the charged aldehyde.

EXAMPLE 54

The preceding Example was repeated except that the isophthalic acid in the second stage dealcoholic thermal decomposition rearrangement of Example 53 was replaced by 10 mol % of benzoic acid, and the reaction temperature was raised to 270° C. Thus 69% of the acetal was converted, and citral was formed in the yield of 41% to the charged aldehyde.

EXAMPLE 55

Example 53 was repeated except that the ammonium sulfate in the first stage reaction was replaced by 0.1 part of p-toluenesulfonic acid. The citral was formed in the yield of 30 mol % to the charged 3-methyl-3-butenal-1.

EXAMPLES 56–58

The following Examples are to show the influence of the ratio of unreacted aldehyde remaining in the reaction mixture from the first-stage acetalization and the acetal formed, on the dealcoholic thermal rearrangement in the second-stage reaction.

25 parts of 3-methyl-3-butenal-1, 15 parts of pulenol, 0.1 part of ammonium sulfate, and 25 vol. parts of benzene were charged in a rotatory band rectification column comprising the reaction zone of 100 vol. parts, and were reacted at 95° C. During the reaction the volume of the system was maintained constant by feeding 10 vol. parts of fresh benzene per hour, and distilling off 10 vol. parts of the water-containing benzene per hour. By varying the reaction time, thus reaction liquids of various aldehyde/unsaturated acetal ratios were formed. To each of the samples an equimolar amount to the ammonium sulfate of sodium carbonate was added, and then 0.01 mol % to the charged aldehyde of methanesulfonic acid was added. Subsequently raising the temperature to 250° C., each system was reacted for 5 minutes. Thus citral was obtained. The ratio of the formed citral to the charged aldehyde in each run was as shown in the table 6.

Table 6

| Example No. | Aldehyde/Unsaturated Acetal Ratio | Citral yield (%) |
|---|---|---|
| 56 | 0.14 | 43 |
| 57 | 0.25 | 39 |
| 58 | 0.43 | 34 |

EXAMPLE 59

2.67 parts of 3-methylbutenal, 5.5 parts of pulenol, 0.001 part of p-toluenesulfonic acid, and 20 vol. parts of benzene were charged to the same rectification column employed in Example 53, and reacted at 90° C. for 2 hours, while the volume of the system was maintained constant by feeding 10 vol. parts of fresh benzene per hour and distilling 10 vol. parts per hour of the water-containing benzene off from the system. Thus 100% of 3-methyl-3-butenal-1 was converted and 3-methyl-3-butenal-1-dipulenylacetal was obtained with the selectivity of 80.2%.

When 80 vol. parts of benzene was added to the reaction liquid and heated for 5 minutes at 250° C., citral was obtained in the yield of 47.9% to the charged aldehyde.

EXAMPLE 60

2.67 parts of 3-methyl-butenal, 26.4 parts of geraniol, 0.001 part of p-toluenesulfonic acid, and 30 vol. parts of benzene were charged in the apparatus similar to that employed in Example 53, and reacted at 98°–102° C. for 2 hours. During the reaction the volume of the system was maintained constant by feeding 10 vol. parts per hour of fresh benzene and distilling 10 vol. parts per hour of the water-containing benzene off from the system. Thus 100% of the 3-methyl-3-butenal-1 was converted, and 3-methyl-3-butenal-1-digeraniol-acetal was obtained with the selectivity of 84.9%.

To the reaction liquid then 174 vol. parts of benzene was added and heated at 250° C. for 5 minutes. Thus farnesol was obtained in the yield of 49.7% to the starting 3-methyl-3-butenal-1.

EXAMPLE 61

To 3.5 parts of 3-methyl-3-butenal diethylacetal, 10 parts of 5-(2,6,6-trimethyl-1-cyclohexene)-3-methyl-2-pentenol and 0.007 part of p-toluenesulfonic acid were added and stirred in nitrogen gaseous current under an aspirator-reduced pressure. The ethanol distilled was caught by the dry ice-methanol-cooled trap. The distillation of thanol ceased after approximately 8 hours reaction. Then 0.003 part of sodium carbonate was added to the reaction product and stirred for approximately 2 hours.

0.05 part of the above product and 0.87 part of benzene were charged in a sealed tube, and reacted at 300° C. for 5 hours, with the following results:

| | |
|---|---|
| Conversion of 3-methyl-3-butenal diethyl acetal | 100% |
| Selectivity for 9-(2,6,6-trimethyl-1- | |
| cyclohexene)-3,7-dimethyl-nonadienal | 34.3%. |

The analysis values of the product, 9-(2,6,6-trimethyl-1-cyclohexene)-3,7-dimethyl-nonadienal, were as follows:

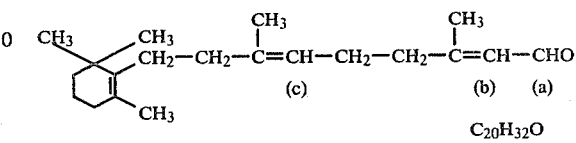

9-(2,6,6-trimethyl-1-cyclohexene)-3,7-dimethyl-nonadienal

| IR spectrum specific absorption | |
|---|---|
| C=C—CHO | νC=O 1675 |
| | νC=C 1630, 1610 |

| NMR spectrum specific absorption | | |
|---|---|---|
| H | τ value | H number |
| H(a) | 0.16–0.31(t) | 1 |
| H(b) | 4.21(d) | 1 |
| H(c) | 4.88–5.04(m) | 1 |

| High mass-data | |
|---|---|
| Calculated | Found |
| C₂₀H₃₂O | C₂₀H₃₂O |
| 288.2456 | 288.2469 |

EXAMPLE 62

Similarly to Example 39, 0.1 part of 3-methyl-3-butenal-1, 0.7 part of crotonyl alcohol and 0.05 mol % of oxalic acid were charged in a sealed tube and reacted at 220° C. for 2 hours. The reaction mixture was analyzed by gas chromatography with the following results;

| | |
|---|---|
| Conversion of 3-methyl-3-butenal-1 | 100% |
| Selectivity of 3-methyl-2.6-octadienal | 17.7% |

EXAMPLE 63

Similarly to Example 53, 2.5 parts of 3-methyl-3-butenal-1, 12.9 parts of crotonyl alcohol, 23 parts of benzene and 0.0017 parts of p-toluenesulfonic acid were charged in a rotary band rectification column, and reacted at 89° C. for 2 hours. During the reaction the volume of the content in the column was maintained constant by feeding 8.7 volume parts per hour of fresh benzene into the column and distilling off 8.7 volume parts of the water-containing benzene per hour. Thus, 100% of the 3-methyl-3-butenal-1 was converted, and 1,1-di-(2-butenyloxy)-3-methyl-3-butene was obtained with the selectivity of 57%.

When 1 part of the product was heated at 250° C. in a sealed tube for 5 minutes together with 0.87 parts of benzene, 80.1% of the acetal was converted, and 3-methyl-2,6-octadienal as the object compound was obtained in the yield of 32.3% to the starting aldehyde.

EXAMPLES 64–66

Twenty (20) parts of 3-methyl-3-butenal-1, 24.3 parts of acetic anhydride, and 0.2 part of sulfuric acid were reacted at room temperature for 2 hours in gaseous current of nitrogen. Thereafter 2 parts of sodium carbonate was added, and the system was distilled in vaquo. Thus 2.4 parts of the product was obtained as the fraction at 77°–78° C./5 mmHg, which was identified to be 1,1-diacetoxy-3-methyl-3-butene, from the results of IR, NMR, and mass spectrum analyses as in the Table 7.

di-(3-methyl-2-butenyloxy)-4-phenyl-3-butene so prepared were shown in Table Q.

0.05 part of thus obtained 1.1-di(-3-methyl-2-butenyloxy)-4-phenyl-3-butene, 0.87 parts of benzene and 0.05 mol % of methane sulfonic acid were charged

Table 7

| Structural Formula | High-mass Data Calculated | Found | IR Spectrum (specific absorption) | NMR Spectrum (specific absorption) | |
|---|---|---|---|---|---|
| (see figure) C₉H₁₄O₄ | C₉H₁₄O₄ 190.0890 | C₉H₁₄O₄ 190.0857 | C—O νC=O 1965  νC=C 1655  δCH 900 | H(a) 3.20–3.31(t)  H(b) 7.59(d)  H(c) 5.20(d) | 1  2  2 |

Thus synthesized 1,1-diacetoxy-3-methyl-3-butene was reacted with pulenol under the reaction conditions indicated in Table 8. Thus formed citral was analyzed by means of gas chromatography, with the results also given in the same Table 8.

in a sealed tube, and after the nitrogen-substitution, the mixture was reacted at 270° C. for 3 minutes. The reaction mixture was analyzed by gas chromatography with the following results;

Table 8

| | | | Reaction condition | | | | Result | |
|---|---|---|---|---|---|---|---|---|
| Example No. | Diacetate (part) | Pulenol (part) | Catalyst (mol %) | Solvent (part) | Temperature (°C.) | Time (min) | Diacetate Conversion | Citral Selectivity |
| 64 | 0.05 | 0.25 | methane sulfonic acid 0.01 | benzene 0.87 | 250 | 40 | 84.7 | 13.8 |
| 65 | 0.05 | 0.25 | PdCl₂ 1 | benzene 0.87 | 250 | 40 | 78.3 | 29.5 |
| 66 | 0.05 | 0.25 | — | benzene 0.81 | 250 | 40 | 84.7 | 5.9 |

EXAMPLE 67

Similarly to Example 1, 1,1-di-(3-methyl-2-butenyloxy)-4-phenyl-3-butene was prepared by an alcohol exchange from 4-phenyl-3-butenal diethylacetal. High mass data, IR spectrum and NMR spectrum of the 1.1-

| | |
|---|---|
| Conversion of 1,1-di-(3-methyl-2-butenyloxy)-4-phenyl-3-butene | 99.6% |
| Selectivity of 4-phenyl-7-methyl-2.6-octadienal | 86.7% |

High mass data, IR spectrum and NMR spectrum of the resulting 4-phenyl-7-methyl-2.6-octadienal were shown in Table Q.

Table Q

| Run No. 18 | Acetal | | The objected product | |
|---|---|---|---|---|
| Structure | [I] Ph—CH=CH—CH₂—CH(O—CH₂—CH=C(CH₃)—CH₃)₂  (d) (c) (b) (a)  (e) (f) | | [II] CH₃—C=CH—CH₂—CH(Ph)—CH=CH—CHO  CH₃  (d)    (c) (b) (a) | |
| | 1.1-di-(3-methyl-2-butenyloxy)-4-phenyl-3-butene C₂₀H₂₈O | | 4-phenyl-7-methyl-2,6-octadienal C₁₅H₁₈O | |
| B.P. °C./mmHg | 153–4/0.25 | | 102/0.3 | |
| High-mass data  Calculated | C₂₀H₂₈O₂ | 300.2092 | C₁₅H₁₈O | 214.1359 |
| Found | C₂₀H₂₈O₂ | 300.2113 | C₁₅H₁₈O | 214.1346 |
| Infrared spectrum (specific absorption | νC=C  νC—O—C  Ph | 1676  1103, 1045, 1010  742, 691 | C=C—CHO  νC=O  νC=C  Ph | 1690  1630  755, 698 |
| NMR spectrum (specific absorption) | τ value  H(a) 5.43–5.55(t) | H number  1 | τ value  H(a) 0.59(d) | H number  1 |

Table Q-continued

| Run No. 18 | Acetal | | | The objected product | | |
|---|---|---|---|---|---|---|
| | H(b) | 7.49–7.62(t) | 2 | H(b) | 3.91–4.18(m) | 1 |
| | H(c) | 3.80–4.08(m) | 1 | H(c) | 3.07–3.30(Q) | 1 |
| | H(d) | 3.62(d) | 1 | H(d) | 4.88–5.06(t) | 1 |
| | H(e) | 6.02(d) | 4 | | | |
| | H(f) | 4.66–4.78(t) | 2 | | | |

-continued

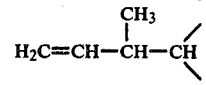 (X-7)

and the moiety (Y) of the compounds of formula (I)

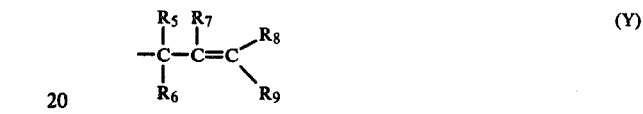 (Y)

We claim:

1. Allyl acetal derivatives of formula (I)

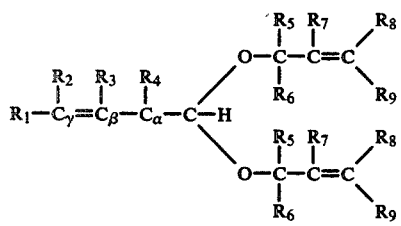 (I)

represents a member selected from the group consisting of:

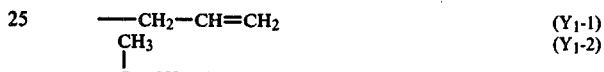 (Y₁-1)

 (Y₁-2)

(Y₁-3)

 (Y₁-4)

 (Y₁-5)

 (Y₁-6)

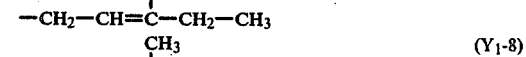 (Y₁-7)

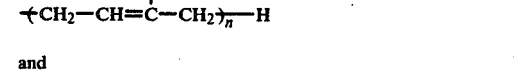 (Y₁-8)

wherein $R_1$ is a hydrogen atom or alkyl group of 1 to 4 carbon atoms, $R_2$ is a hydrogen atom, $R_3$ and $R_4$ may be the same or different and each represents a hydrogen atom or methyl group, $R_5$, $R_6$, $R_7$ and $R_8$ may be the same or different and each represents a hydrogen atom or methyl group, and $R_9$ is a hydrogen atom, saturated aliphatic hydrocarbon group of 1 to 16 carbon atoms or unsaturated aliphatic hydrocarbon group of 2 to 11 carbon atoms.

2. The allyl acetal derivatives of claim 1 wherein the moiety (X) of the compounds of formula (I)

$$R_1-C_\gamma=C_\beta-C_\alpha-C-H \quad (X)$$

is selected from the group consisting of

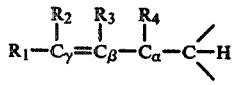 (X-1)

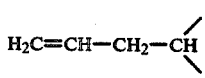 (X-2)

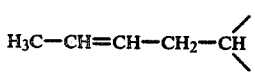 (X-3)

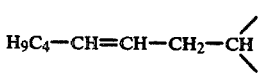 (X-6)

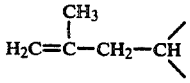

and and (Y₁-9)

wherein in the formula (Y₁-8) and (Y₁-9) n=1-2.

3. The allyl acetal derivative of claim 1 which is selected from the group consisting of
1,1-di-(3-methyl-2-butenyloxy)-3-methyl-3-butene,
1,1-di-(3-propenyloxy)-3-methyl-3-butene,
1,1-di-(2-methyl-2-propenyloxy)-3-methyl-3-butene,
1,1-di-(2-butenyloxy)-3-methyl-3-butene,
1,1-di-(3,7-dimethyl-2,6-octadienyloxy)-3-methyl-3-butene,
1,1-di-(3,7,11-trimethyl-2,6,10-dodecatrienyloxy)-3-methyl-3-butene,
1,1-di-(3,7,11,15-tetramethyl-2-hexadecenyloxy)-3-methyl-3-butene,
1,1-di-(2-methyl-2-butenyloxy)-3-methyl-3-butene,
1,1-di-(1-methyl-2-propenyloxy)-3-methyl-3-butene,
1,1-di-(3-methyl-2-butenyloxy)-3-butene,
1,1-di-(2-methyl-2-propenyloxy)-2-methyl-3-butene,
1,1-di-(3-methyl-2-butenyloxy)-3-octene, and
1,1-di-(pentyloxy)-3-methyl-3-butene.

4. The allyl acetal derivative of claim 1 which is 1,1-di-(3-methyl-2-butenyloxy)-3-methyl-3-butene.

5. The allyl acetal derivatives of claim 1 wherein $R_3$ is methyl.

* * * * *